(12) United States Patent
Brodie et al.

(10) Patent No.: US 10,332,735 B2
(45) Date of Patent: Jun. 25, 2019

(54) SAMPLE PREPARATION APPARATUS AND METHOD FOR ELEMENTAL ANALYSIS SPECTROMETER

(71) Applicant: Thermo Fisher Scientific (Bremen) GmbH, Bremen (DE)

(72) Inventors: Christopher Brodie, Bremen (DE); Oliver Kracht, Bremen (DE); Alexander Hartwig, Bremen (DE); Michael Krummen, Bad Zwischenahn (DE); Johannes Schwieters, Genderkesee (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 0 days.

(21) Appl. No.: 15/690,617

(22) Filed: Aug. 30, 2017

(65) Prior Publication Data

US 2018/0076013 A1    Mar. 15, 2018

(30) Foreign Application Priority Data

Sep. 2, 2016 (GB) .................... 1614952.8

(51) Int. Cl.
*H01J 49/04* (2006.01)
*G01N 30/30* (2006.01)
(Continued)

(52) U.S. Cl.
CPC .......... *H01J 49/0468* (2013.01); *G01N 30/12* (2013.01); *G01N 30/30* (2013.01);
(Continued)

(58) Field of Classification Search
CPC ...... G01N 30/30; G01N 30/40; G01N 30/463; G01N 30/62; G01N 30/68; G01N 30/7206;
(Continued)

(56) References Cited

U.S. PATENT DOCUMENTS 3,096,157 A * 7/1963 Brown ................... G01N 30/06
422/89
4,054,414 A 10/1977 Grob et al.
(Continued)

FOREIGN PATENT DOCUMENTS

CN    101871922 A    10/2010
GB    2358924 A    8/2001
(Continued)

OTHER PUBLICATIONS

Hansen et al., "Increasing the sensitivity of δ13C and δ15N abundance measurements by a high sensitivity elemental analyzerconnected to an isotope ratio mass spectrometer", Rapid Commun. Mass Spectrom. 2007, 21, pp. 314-318.
(Continued)

*Primary Examiner* — David A Vanore
(74) *Attorney, Agent, or Firm* — David A. Schell

(57) ABSTRACT

A sample preparation apparatus for an elemental analysis system comprising a sample combustion and/or reduction and/or pyrolysis arrangement for receiving a sample of material to be analyzed, and producing therefrom a sample gas flow containing atoms, molecules and/or compounds; a gas chromatography (GC) column into which the sample gas flow is directed; a heater for heating at least a part of the GC column; and a controller for controlling the heater. The controller is configured to control the heater so as to increase the temperature of at least the part of the GC column while the sample gas flow in the GC column elutes.

21 Claims, 19 Drawing Sheets

(51) Int. Cl.
*H01J 49/42* (2006.01)
*G01N 30/12* (2006.01)
*G01N 30/72* (2006.01)
*B01D 59/44* (2006.01)
*G01N 31/12* (2006.01)

(52) U.S. Cl.
CPC ...... *G01N 30/7206* (2013.01); *H01J 49/0422* (2013.01); *H01J 49/426* (2013.01); *B01D 59/44* (2013.01); *G01N 31/12* (2013.01); *G01N 2030/125* (2013.01); *G01N 2030/3076* (2013.01)

(58) Field of Classification Search
CPC ..... G01N 2030/121; G01N 2030/0095; G01N 2030/3007; G01N 2030/3061; G01N 2030/3076; G01N 2030/8417; G01N 2030/025; G01N 2030/122; G01N 2030/3038; G01N 2030/3046; G01N 2030/3053; G01N 2030/3069; G01N 2030/3084; G01N 2030/383; G01N 2030/402; G01N 2030/405; G01N 2030/623; G01N 2030/8886; G01N 33/225; G01N 29/022; G01N 29/2462; G01N 27/622; G01N 25/32; G01N 25/22
USPC .......... 422/89, 51, 94; 374/36, 37; 73/23.35, 73/23.369, 23.42
See application file for complete search history.

(56) References Cited

U.S. PATENT DOCUMENTS

| | | | |
|---|---|---|---|
| 4,650,499 A | 3/1987 | Scott | |
| 5,141,534 A * | 8/1992 | Sacks | G01N 30/12 96/102 |
| 5,437,179 A * | 8/1995 | Wiegand | G01N 30/30 73/23.35 |
| 5,816,705 A * | 10/1998 | Vander Heyden | G01N 25/22 374/37 |
| 6,423,120 B1 * | 7/2002 | Nickerson | G01N 30/30 210/198.2 |
| 6,481,263 B1 * | 11/2002 | Haley | G01N 27/622 250/287 |
| 7,708,943 B1 * | 5/2010 | Robinson | G01N 33/225 422/51 |
| 2006/0008385 A1 * | 1/2006 | Millor, II | G01N 30/30 422/89 |
| 2008/0289397 A1 * | 11/2008 | Hassan | G01G 3/16 73/23.4 |
| 2009/0314057 A1 | 12/2009 | Hatscher et al. | |
| 2011/0212536 A1 | 9/2011 | Krummen et al. | |
| 2012/0085148 A1 * | 4/2012 | Amirav | G01N 30/30 73/23.39 |
| 2012/0123582 A1 | 5/2012 | Jasper | |
| 2016/0320362 A1 | 11/2016 | Schwieters et al. | |
| 2018/0076013 A1 * | 3/2018 | Brodie | H01J 49/0468 |

FOREIGN PATENT DOCUMENTS

| | | |
|---|---|---|
| GB | 2370517 A | 7/2002 |
| GB | 2537915 A | 11/2016 |
| WO | 99/52127 A2 | 10/1999 |

OTHER PUBLICATIONS

Hansen et al., "Simultaneous d15N, d13C and d34S measurements of lowbiomass samples using a technically advanced high sensitivity elemental analyzer connected to an isotope ratio mass spectrometer", Rapid Commun. Mass Spectrom. 2009 (23), pp. 3387-3393.

* cited by examiner

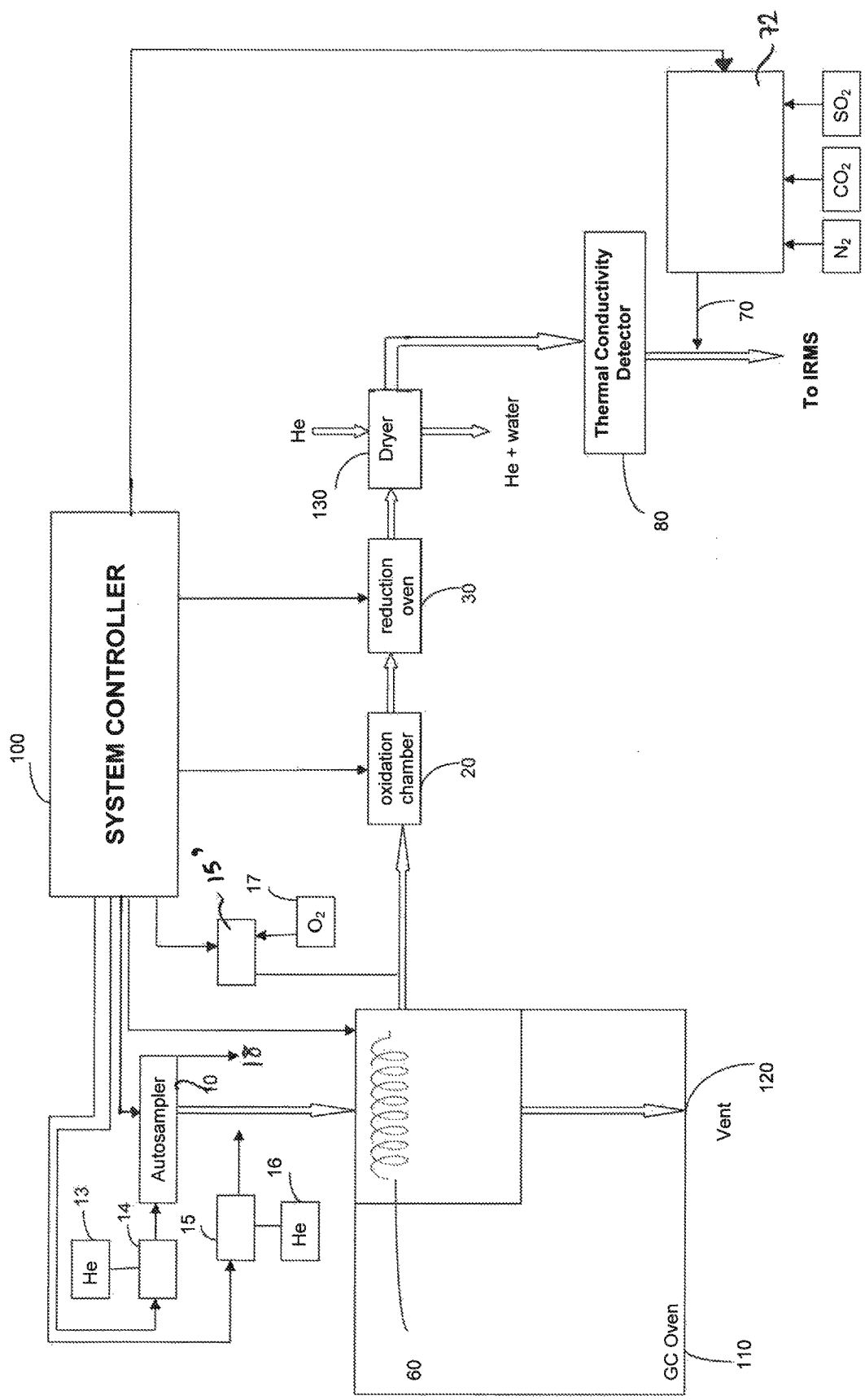
Figure 1b – PRIOR ART

SAMPLE PREPARATION APPARATUS AND METHOD FOR ELEMENTAL ANALYSIS SPECTROMETER

FIELD OF THE INVENTION

This invention relates to an improved sample preparation apparatus for an elemental analysis system such as an elemental analysis isotope ratio mass spectrometer (EA-IRMS). The invention is particularly but not exclusively suitable for simultaneous $\delta^{13}C$, $\delta^{15}N$ and $\delta^{34}S$ measurements and % C, % N and % S determinations in such a spectrometer.

BACKGROUND TO THE INVENTION

Isotope Ratio Mass Spectrometry (IRMS) is a technique that finds application across many fields including geosciences, archaeology, medicine, geology, biology, food authenticity and forensic science. Accurate and precise measurement of variations in the abundances of isotopic ratios of light elements in a sample such as $^{13}C/^{12}C$ ($\delta^{13}C$), $^{15}N/^{14}N$ ($\delta^{15}N$), $^{18}O/^{16}O$ ($\delta^{18}O$), D/H, and $^{34}S/^{32}S$ ($\delta^{34}S$), relative to an isotopic standard, can provide information on the geographical, chemical and biological origins of substances, allowing differentiation between samples that are otherwise chemically identical. The $\delta$ values are defined in a specific way. For example, $\delta^{13}C$ is defined as:

$$\delta^{13}C(0/00) = \left(\frac{\left(\frac{^{13}C}{^{12}C}\right)_{sample}}{\left(\frac{^{13}C}{^{12}C}\right)_{isotopic\ standard}} - 1\right) * 1000$$

A typical EA-IRMS instrument is formed of six main sections: a sample introduction system, a sample preparation system, an electron ionisation source, a magnetic sector analyser, a Faraday collector detector array, and a computer controlled data acquisition system. The sample is split into atoms/molecules and/or compounds by the sample preparation system. The electron ionisation source ionizes the prepared sample and the resulting sample ions are spatially separated in the magnetic sector analyser. The Faraday collector comprises a detector array which detects the spatially separated ions, and the computer controlled data acquisition system generates mass spectra from the Faraday collector outputs.

Sample preparation may be achieved in a number of different ways, with advantages and disadvantages to each. The two best-known groups of techniques for sample preparation are those which carry out elemental analysis for the whole sample (EA-IRMS), and those which first separate the chemical substances of the sample by gas chromatography before splitting the separated substances into atoms/molecules and/or compounds (GC-IRMS). Liquid chromatography (LC-IRMS) has also been explored for sample preparation but is less commonly used.

EA-IRMS is a measurement technique which analyses the whole sample at the same time, to investigate the variations in the abundances of isotope ratios in the whole sample. FIG. 1a shows a highly schematic arrangement of the sample introduction and preparation part (see above) of an EA-IRMS system. The system is under the control of a system controller 100 as may be seen.

A sample (not shown in FIG. 1a) is weighed and placed in a combustible capsule (also not shown in FIG. 1a). The combustible capsule is sealed with the sample inside and is usually made of tin, although aluminium or silver may be used instead.

An autosampler carousel 10 is positioned above a combustion furnace 20. Helium purge gas is supplied to the autosampler 10, typically at a rate of 20-300 ml/min, by a first gas supply control 14 from a first Helium bottle 13 to reduce air intake. The He purge gas flows out of the sampler via the outlet pipe 18. The autosampler carousel 10 injects the sealed sample capsule into the combustion furnace 20 in a carrier gas flow of helium supplied by a second gas supply control 15 from a second Helium bottle 16. The sample is combusted in the combustion furnace 20, under the control of the system controller 1. Pulsed oxygen may optionally be employed to aid combustion. The oxygen is supplied from an oxygen bottle 17, also under the control of the second gas supply control 15.

The sample matrix breaks down into its constituent elemental components (mostly atoms) and is conveyed by the carrier gas flow of Helium from the second Helium bottle 16, across an oxygen donor compound such as $Cr_2O_3$, $WO_3$, or CuO. The oxygen donor is present to ensure complete oxidation of the elemental components, particularly of carbon, nitrogen and sulfur evolved from the sample matrix. Typically the reactor zone (containing the oxygen donor) in the combustion furnace 20 is held at a temperature of between 400 and 1100 degrees Celsius, with an ideal range of between 900 and 1050 degrees Celsius. The Helium carrier gas employs a maximum flow rate of up to 1000 mL/min, but typically in the range of 40 to 200 mL/min.

The resulting products may be one or more of $NO_x$, $CO_2$, $SO_2$ and/or $H_2O$. After the oxidation a reduction takes place. For example, to measure $\delta^{15}N$, $NO_x$ has to be reduced to $N_2$. This may be carried out either using separate, serially arranged combustion and reduction furnaces (as shown in FIG. 1a), or alternatively by combining both into a single reactor heated by the same furnace.

In particular, the arrangement shown in FIG. 1a, employs a separate reduction oven 30, arranged downstream of the combustion furnace 20 and heated separately to the combustion furnace 20. In the arrangement of FIG. 1a, the sample is generally swept across the oxygen donor material in the reactor zone of the combustion furnace 20 using the Helium carrier gas, and then transferred to the reduction oven 30, via a stainless steel/sulfinert capillary or heated bridge, which contains metallic copper (not shown in FIG. 1a). The reduction oven 30 is generally held at a temperature between 450-900° C. and is designed to reduce $NO_x$ and NO gas species (for example) to $N_2$, reduce $SO_3$ to $SO_2$ and absorb excess $O_2$ not used in the combustion reaction.

In the alternative arrangement, where the combustion and reduction processes may instead be combined in the same reactor, heated by the same furnace, the analyte gases first pass across the oxygen donor compound. The gases are then conveyed onward to metallic copper within the same reactor. Here, they undergo the same chemical reaction as described above in respect of the serially arranged furnaces illustrated in FIG. 1a.

In either case (separate or combined combustion and reduction furnaces/ovens), the resultant gases are then directed through a moisture trap 50 (FIG. 1a). Optionally, a chemical trap 40 can also be provided, which may contain soda lime, NaOH on a silica substrate, Carbosorb® or the like. The chemical trap 40 may allow removal of carbon dioxide from the analyte gases when it is only desired to look at nitrogen isotope ratios. The moisture trap 50 usually contains Magnesium perchlorate to trap any water generated during the combustion process. Depending upon the nature of the reagents, the chemical trap 40 and moisture trap 50 may be placed in the reverse order to that shown in FIG. 1*a*.

The dried gaseous output is introduced into a separation column 60 that serves to separate the output into its constituent atoms, molecules or compounds, e.g. carbon dioxide and nitrogen or carbon dioxide, nitrogen and sulphur dioxide. The separation column 60 may be a packed column for gas chromatography (GC) having a constant temperature when the dried gaseous output flows through the GC column, the GC column being heated by a resistance heater 62 surrounding the GC column 60. The resistance heater 62 is controlled by a heater controller 68 to keep the temperature of the GC column constant. This heater controller 68 is triggered to start the heating by the system controller 100. The arrangement of FIG. 1*a* shows a separation column 60 in the form of a GC column, with the moisture trap 50 arranged before the separation column 60 as described above.

Once the analyte gas has been separated into its combustion components based on their interaction with the separation column 60, they are conveyed through a thermal conductivity detector (TCD) 80, which forms the basis of weight % determinations. Detection by the TCD 80 is non-destructive. Therefore, after detection, the gas can be conveyed to an isotope ratio mass spectrometer, via an interface capable of diluting the gas if required (not shown in FIG. 1*a*), for simultaneous measurement, in particular of $\delta^{13}C$, $\delta^{15}N$ and/or $\delta^{34}S$ values.

Before or after the measurement of an isotope ratio by IRMS, or in parallel with the measurement of an isotope ratio by IRMS, a reference gas of the investigated isotope ratio can be supplied to the IRMS in order to allow a reference measurement to be carried out. The reference gas may be supplied via a gas supply pipe 70 and is under the control of a reference gas supply controller 72 The reference gas supply controller 72 is connected with a bottle 73 of $N_2$, a bottle 74 of $CO_2$ and a bottle 75 of $SO_2$. The measured isotopic ratio is an average for the whole sample. EA-IRMS is particularly suited to non-volatile substances such as soils, sediments, plants, foods, drugs, amino and fatty acids, and many more. Although an average isotope ratio value for the whole sample is obtained, nevertheless analysis of very small samples is possible.

The separation column 60 could also be a thermal desorption unit for gas separation. In such a desorption unit, the thermal desorption temperature is varied as described in EP-A-1 831 680. If the separation column is instead a thermal desorption unit, the moisture trap 50 may be also arranged after the separation column 60.

The thermal desorption unit uses the principle of thermal desorption. Gases emerging from the reduction oven are supplied to the desorption unit. The entire mixture of components of the gas is adsorbed by the adsorbing material of the thermal desorption unit. This adsorption takes place at temperatures between room temperature and 50 degrees Celsius, in systems having a single thermal desorption unit (systems having multiple thermal desorption units are also known, and in these, the lower end of the temperature range may be above room temperature).

The whole gas is stored and can be concentrated by the adsorbing material. Separation of the components of the gas takes place based on different desorption temperatures. Thus, the thermal desorption unit has to be heated to various temperatures to supply specific components of the gas to the EA-IRMS. Due to the control of the desorption of specific elements by the heating temperature it is possible to control the time of the supply of specific component of the gas to the EA-IRMS and the time between the supply of two specific component of the gas to EA-IRMS to be analysed.

GC-IRMS, by contrast, permits separation of the sample prior to isotope ratio analysis. This in turn permits isotopic analysis of complex mixtures by a specific isotope analysis of each chemical substance contained in the mixture, which can reveal additional information not normally available using EA-IRMS, as well as better discrimination. FIG. 1*b* shows a typical arrangement of a GC-IRMS system, again in highly schematic form. Components common to FIGS. 1*a* and 1*b* are labelled with like reference numbers.

Liquid samples (not shown) are provided in small vials (not shown) and loaded into an autosampler 10. The samples are injected by the autosampler 10 into a gas chromatograph (GC) column 60 e.g. by a syringe system (not shown). The gas chromatograph (GC) 60 can be heated in a GC oven 110 under the control of a system controller 100 to improve the separation of the chemical substances contained in the mixture of the investigated sample. The GC oven 110 includes a vent 120. The sample elutes from the column of the GC 60 into an oxidation chamber 20, such as a non-porous alumina tube, usually mounted on the side of the GC oven 100. The eluents from the GC 60 are combusted at elevated temperatures e.g. into $NO_x$, $CO_2$, and/or $H_2O$. As with the EA-IRMS of FIG. 1*a*, to measure e.g. $\delta^{13}C$, the resulting products are carried in a stream of dry Helium through a reduction oven 30 that converts the nitrous oxides into $N_2$ and removes any excess $O_2$. Water (which is a byproduct of the combustion) is removed using a counter-flow of dry helium in a dryer 130, and the dried gaseous output may be introduced into a Thermal Conductivity Detector (TCD) 80.

The gases exiting the TCD 80 are carried into an IRMS (again not shown in FIG. 1*b*) using $CO_2$ from a reference $CO_2$ supply 70 that is introduced at an open split.

As with the arrangement of FIG. 1*a*, various components in FIG. 1*b* are under the control of the system controller 100. The system controller 100 controls the autosampler 10 as it supplies a sample to the combustion oven 20, triggers the supply of the purge gas to the autosampler 10 via the first gas supply control 14, and triggers the supply of the carrier gas flow and the (optional) combustion-assisting oxygen pulse via the second gas supply control 15. The system controller also sets the set-points of the temperature of the combustion oven 20 and the temperature of the reduction oven 30. Finally the system controller 100 controls the temperature of the GC oven 110 which heats the GC column 60. As noted above, EA-IRMS and GC-IRMS are complementary techniques. GC-IRMS allows a specific analysis of each chemical substance contained in a sample, e.g. an organic matter sample (for example, individual amino acids in a protein), but requires that any compound constituting the sample mixture can be made sufficiently volatile and thermally stable to permit initial elution in a GC. It also allows analysis of very small sample quantities (nanogram to picogram range; the typical sample weight in an EA-IRMS experiment is in the milligram to microgram range). The main drawbacks of GC-IRMS are the considerably longer analysis time (typically hours rather than minutes as with EA-IRMS), loss of sample integrity during sample preparation, cost and user complexity. Due to the separation of the chemical substances of the sample by the GC column, the different atoms, molecules and/or compounds of each separated chemical substance are supplied to the mass analyser simultaneously during the GC-IRMS measurement. The different atoms, molecules and/or compounds such as $N_2$, $CO_2$ and $SO_2$ of each chemical substance are very difficult to resolve in such systems. Therefore the measurement results of GC-IRMS are much more complex, or on the other hand different isotope ratios have to be measured one after the other which is very time consuming.

The present invention relates to EA-IRMS, which allows isotopic analysis of the whole samples. One of the key benefits of EA-IRMS is the relatively short time needed for sample analysis. In recent years, simultaneous $\delta^{13}C$, $\delta^{15}N$ and $\delta^{34}S$ measurements have become a more common approach in EA-IRMS across all application fields. This is because of the ability to produce accurate and precise data from one sample drop, thus increasing system productivity and reducing sample analysis costs. However, such simultaneous measurements in EA-IRMS present a number of challenges. FIG. 2 illustrates a chromatogram for simultaneous $\delta^{13}C$, $\delta^{15}N$ and $\delta^{34}S$ analysis of sulfanilamide using GC separation at a constant temperature (isothermal) in an EA-IRMS experiment such as that described in connection with FIG. 1a above.

Carbon dioxide, nitrogen and sulfur dioxide molecules generate peaks in the chromatogram of FIG. 2. These molecules are contained in the dried gaseous output of the moisture trap 50 after a sample has been introduced into the sample introduction system shown in FIG. 1a. To the left of FIG. 2, mass peaks of $N_2$ molecules (having isotopic masses 28 u (peak 128) and 29 u (peak 129)) may be observed. The mass peaks of $CO_2$ molecules having isotopic masses 44 u (peak 244), 45 u (peak 245) and 46 u (peak 246) are also visible in FIG. 2. Mass peaks of $SO_2$ molecules having isotopic masses 64 u (peak 364) and 66 u (peak 366) may be seen towards the right of FIG. 2. To determine the isotope ratios $\delta^{13}C$, $\delta^{15}N$ and $\delta^{34}S$, reference gases are supplied to the IRMS via the gas supply 70 in parallel with the measurement of the molecules originating from the investigated sample. Those peaks in the chromatogram arising from reference gases are labelled with the same reference number as the corresponding sample gas peak, save for the addition of a prefixed "R". So, for example the peak labelled "128" in FIG. 2 represents the mass peak of $N_2$ molecules having the isotopic mass 28 u, and which originate from the investigated sample. The peak of $N_2$ molecules having the isotopic mass 28 and which are derived from the $N_2$ reference gas is labelled with the reference number "R128".

The chromatogram of FIG. 2 exhibits relatively poor $N_2$ and $CO_2$ separation (less than 10 seconds, with some loss of $N_2$ peak tail), a high peak width for $SO_2$ (greater than 100 seconds) and long retention time of $SO_2$, which is the time the $SO_2$ need to pass the GC column, resulting in a total analysis time of in excess of 15 minutes, although this time can often be even longer. The GC column is held at a temperature of around 65-80 degrees Celsius, in the experiment in which the FIG. 2 data are derived and is based on a sample of sulfanilamide (C/S ratio of around 2.5). Sufficient baseline separation between $N_2$ and $CO_2$ on the one hand, and $CO_2$ and $SO_2$ is particularly challenging in samples with large $CO_2$ amounts relative to $N_2$ and $SO_2$. For example, analysis of high C/S ratio samples, such as wood (>5000:1), would result in chromatographic separation compromises that would make the analysis using an isothermal technique impossible for $\delta^{13}C$, $\delta^{15}N$ and $\delta^{34}S$ from a single sample drop, because separation of $N_2$ and $CO_2$ peaks would not be achieved, and the $SO_2$ peak shape for small S concentrations would result in poor reproducibility.

So the $CO_2$ peaks, the $N_2$ peaks and the $SO_2$ peaks show a peak tailing, that is, exhibit peaks that are not very sharp on their tail side. Sharp peaks permit better peak separation, particularly for the $N_2$ peaks and the $CO_2$ peaks, because the tail side of the $N_2$ peaks do not then extend so close to the front side of the $CO_2$ peaks. Also, for peaks that do not exhibit peak tailing, data integration of the peak is better, and determination of the ratio of the various isotopes is improved. This improvement arises particularly from the fact that, for sharp peaks, it is much easier to distinguish the noise measured in an measurement signal of an EA-IRMS, from the signal of a peak. This results in a more accurate data integration of the peak and consequently a more accurate determination of the ratio of the various isotopes measured by the peak. By contrast, peak tailing results in an extension of the measuring time.

It is possible to reduce the analysis time slightly by operating the GC column at a higher constant temperature, in some prior art systems. However, raising the temperature of the GC column results in poorer $N_2$ and $CO_2$ separation. Thus there is a compromise between achieving analytically acceptable data and the time taken to obtain that. To date, an optimal compromise of around 18 minutes per simultaneous NCS analysis, per sample, has been employed.

The alternative, which is to analyse each of $\delta^{13}C$, $\delta^{15}N$ and $\delta^{34}S$ separately, has its own drawbacks, in terms of an increase in initial sample weighing and preparation time, along with a requirement for at least three times the amount of the sample. In fact, some prior art EA-IRMS systems require repetition of an experiment once or twice before a statistically acceptable accuracy of the data can be achieved. In such cases, attempting to analyse $\delta^{13}C$, $\delta^{15}N$ and $\delta^{34}S$ separately can in fact result in up to 6 times more analyses than a simultaneous $\delta^{13}C$, $\delta^{15}N$ and $\delta^{34}S$ analysis. This results in additional costs per analysis, a longer overall sample preparation time, and lower system productivity (that is, a lower throughput of a specific sample).

Various solutions to these problems have been proposed. One solution employs two GC columns, an S column for the $SO_2$, and an NC column for the $N_2$ and $CO_2$ molecules. The dried gaseous output of a moisture trap 50, containing of $N_2$, $CO_2$ and $SO_2$, flows initially into the S column. The gas flow downstream of the S column can be switched by way of a valve. The valve is initially in a first position which directs the gas flow out of the S column directly to the IRMS, in order that it may be analysed thereby. Once the $SO_2$ has passed through the S column, the valve is switched into a second position so that the gas flowing out of the S column is instead directed next to the NC column. The gas flow out of the NC column is then directed to the IRMS to be analysed. Using this arrangement, the sequence of the molecules to be analysed is changed: initially the $SO_2$ peak is measured by the IRMS, and subsequently the $N_2$ and $CO_2$ peaks are measured by the IRMS. Measurement time can be reduced by the use of a shorter column length of the S column, and larger quantities of $CO_2$ can be measured. Overall, however, the measurement time for the method may be increased, because (at least for a part of the analysis period), the gas is required to flow through two columns (the S and the NC columns) before being measured. Moreover, the costs for this arrangement are higher because of the use of two GC columns as well as an additional controlling system for controlling the additional switching valve.

Also the use of a thermal desorption unit as separation column 60 has its disadvantages. A process of continuously flowing gas into the separation column 60 is not employed. Instead, it is necessary initially to adsorb the whole mixture of gases to be analysed, with the separation column 60 at a low temperature. Only then, by controlled elevation of the temperature, are the specific components to be analysed set free (by a process of desorption) and supplied to the EA-IRMS. This process is time consuming and more difficult to control. Also, the accuracy of the measurement suffers, because it is possible that the specific elements to be analysed are not completely adsorbed during the initial phase of analysis, so that they cannot subsequently be desorbed.

The present invention seeks to address these challenges with existing EA-IRMS devices and methods. It is one of the objects of the invention to reduce the measurement time for the elemental analysis system. It is another one of the objects of the invention to improve the distance between the peaks of different atoms, molecules and/or compounds in the measurement results of the elemental analysis device and to achieve a better peak separation. It is still another one of the objects of the invention to improve the peak shape of the detected atoms, molecules and/or compounds by minimising peak tailing and reducing the peak width. It is still another one of the objects of the invention to expand the range of sample types that may be analysed; for example, it is an object to permit analysis of samples having a high C/S value such as wood. It is still another one of the objects of the invention to reduce the experimental costs associated with the elemental analysis system, for example by reducing the amount of the investigated sample that is needed for successful analysis, and/or by reducing the amount of the flow gases that are needed.

SUMMARY OF THE INVENTION

According to a first aspect of the present invention, there is provided a sample preparation apparatus for an EA-IRMS, in accordance with claim 1.

The invention also extends to an EA-IRMS apparatus including such a sample preparation apparatus.

In another aspect of the invention, there is provided an EA-IRMS method.

By increasing the GC temperature according to a temperature gradient during analysis, many of the problems of the prior art EA-IRMS techniques are avoided or at least ameliorated. For example, when the GC temperature is held static during simultaneous $\delta^{13}C$, $\delta^{15}N$ and $\delta^{34}S$ analysis, the chromatographic peaks are not as sharp as desired and do not exhibit the lowest possible retention times. Peak tailing can also be exaggerated, especially for sulphur dioxide.

A GC temperature profile with a temperature gradient, by contrast, can optimize data integration, improve the determination of isotope ratios, and lower sample analysis times. In particular, increasing the temperature of the GC during analysis can reduce the data acquisition time and achieve complete separation of $N_2CO_2$ and $SO_2$, with sharp peak shapes and lower retention times, resulting in accurate and precise data. The temperature gradient GC technique makes it possible to investigate samples with a high content of carbon atoms.

The method and apparatus of the present invention desirably employ a continuous flow of gas into the GC column to which the temperature gradient is applied. This is in contrast to a thermal desorption unit, when it is used as separation column 60. If the temperature of at least a part of the GC column is increased whilst the sample gas flow in the GC column elutes, it has been found that the elution time of the atoms, molecules and/or compounds contained in the sample gas flow can be changed. In consequence, it is possible to change the chronological distance between two peaks of different atoms, molecules and/or compounds contained in the sample gas flow as they leave the GC column. The result is both a change in the chronological distance between the centre of the peaks, and a change in the chronological distance between the peaks, where no peak is detected. As a further benefit, some of the atoms, molecules and/or compounds contained in the sample gas flow leave the GC column after a relatively shorter time period. This decreases the measurement time for some experiments considerably.

For example, to date, when the dried gaseous output of a moisture trap 50 flows, as a sample gas flow, through a GC column held at a constant temperature, there are markedly different speeds of elution of $N_2$ and $CO_2$ on the one hand, and $SO_2$ on the other. It has been found that, by increasing the temperature of the GC column whilst the sample gas flow in the GC column elutes, the $SO_2$ peak can be expected much sooner. It has also been found that, by increasing the temperature of the GC column whilst the sample gas flow in the GC column elutes, the chronological distance between the $N_2$ peaks and $CO_2$ peaks where no peak is detected, is increased.

It has still further been found that, by increasing the temperature of at least a part of the GC column whilst the sample gas flow in the GC column elutes, the peak shape of atoms, molecules and/or compounds contained in the sample gas flow detected by the IRMS can be changed in a manner such that the shape of the peaks is sharpened. Peak tailing can in particular be reduced or avoided. This improves the data integration of the peak and the determination of the ratio of the isotopes to be detected, whether by the use of an elemental analysis system such as an IRMS, by the use of a thermal conductivity detector, or otherwise. The reduced or removed peak tailing allows peaks that have been eluted in rapid succession to be better distinguished by the elemental analysis system (IRMS, thermal conductivity detector or otherwise).

For example, it has been found that increasing the temperature of the GC column whilst the sample gas flow in the GC column elutes results in an improvement in the peak shapes of $N_2$, $CO_2$ and $SO_2$ when they are in the sample gas flow. Due to the applied temperature gradient, the peaks appear sharper and the peak tailing of the peaks can be reduced significantly and sometimes totally. So the $N_2$ peaks and $CO_2$ peaks can be better distinguished. This results in an increase of the chronological distance between the $N_2$ peaks and $CO_2$ peaks where no peak is detected.

In an embodiment, the GC temperature profile may be such that for a first time period there may be a first fixed temperature, $T_{start}$, whilst during a second time period there may be a second fixed temperature $T_{end}$. Between these times the temperature is increased. The rate of ramping of the temperatures in the GC may be linear or non-linear, ie, $\theta T/\theta t$ may be constant or variable. The result is a system and method offering higher system productivity through greater sample throughput, and accurate and precise analysis isotope ratios like $\delta^{13}C$, $\delta^{15}N$ and $\delta^{34}S$. A single sample drop can be employed, whereas, with prior art isothermal GC analysis, often the experiment must be carried out twice or three times using additional material from the same sample, in order to achieve an acceptable accuracy level. Thus embodiments of the present invention permit a significant workflow enhancement in the form of a reduction in the cost per sample analysis.

Preferred embodiments of the invention also allow a data acquisition time reduction of at least 30-40% relative to the time taken in the traditional isothermal GC approach. For example, the typical 18-minute data acquisition time (a result of the trade-off between acquisition time and peak shape/baseline separation explained in the Background section above) with an isothermal GC, may be reduced to as low as 9 minutes. A desirable consequence of the reduction in acquisition time is a reduction in the amount of helium gas required for sample purge and drying and as flow gas during analysis.

Although the technique is useful in respect of samples having a wide variety of ratios of N:C:S, it is particularly attractive when seeking to analyse samples having high (eg, 5000 or greater) ratios of carbon to sulphur.

BRIEF DESCRIPTION OF THE DRAWINGS

The invention may be put into practice in a number of ways and some specific embodiments will now be described by way of example only and with reference to the accompanying drawings in which:

FIG. 1b shows, again highly schematically, an arrangement of a part of a prior art gas chromatography isotope ratio mass spectrometer (GC-IRMS);

FIG. 3b shows a highly schematic arrangement for varying the temperature of the GC column in FIG. 3a;

FIG. 6 shows a first exemplary temperature profile that may be applied to the temperature varying GC column of FIG. 3a;

FIG. 9 shows a second exemplary temperature profile that may be applied to the temperature varying GC column of FIG. 3a;

DETAILED DESCRIPTION OF PREFERRED EMBODIMENTS

Figure 3A:
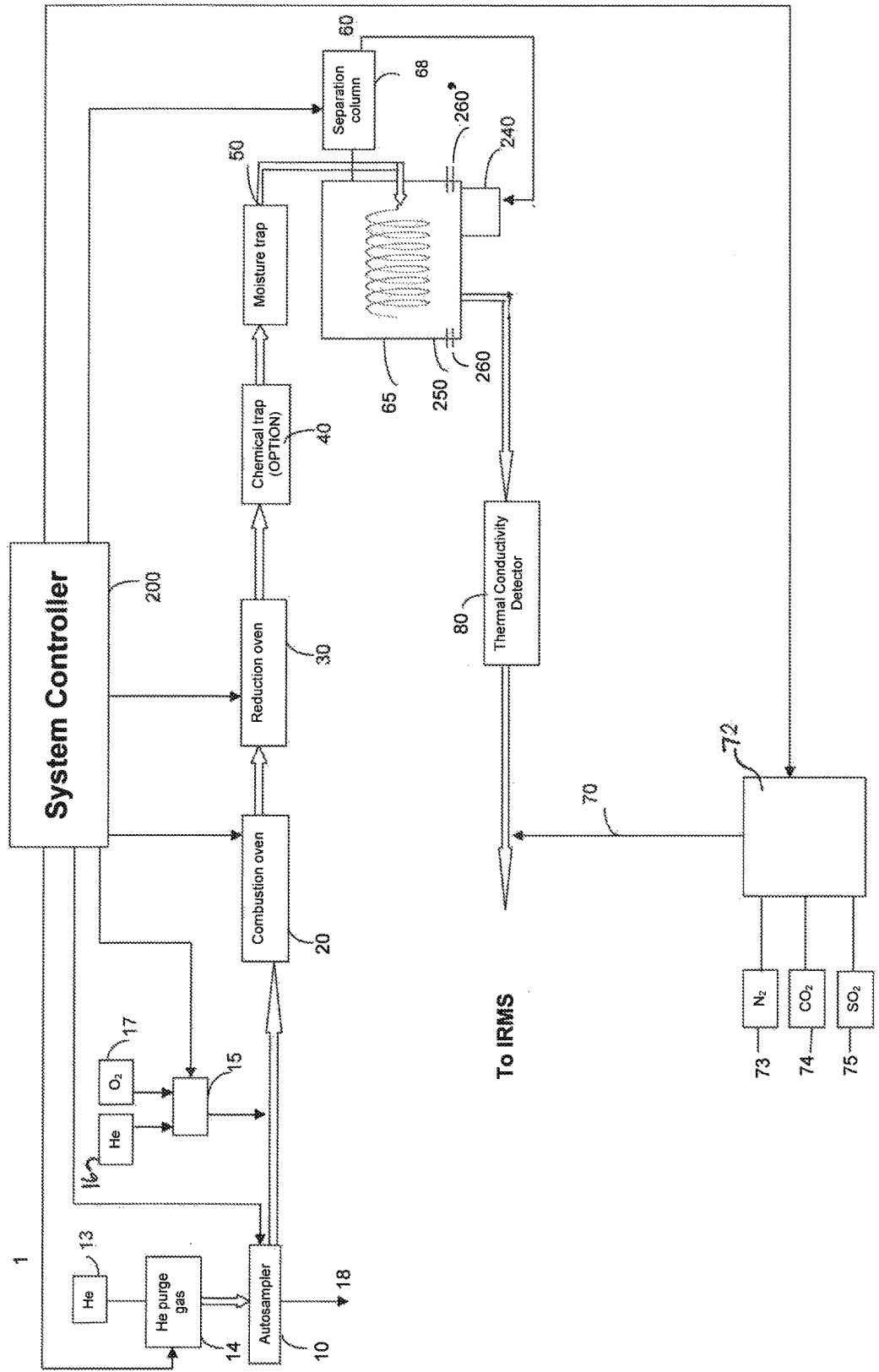
FIG. 3a shows a highly schematic arrangement of a sample preparation section of an EA-IRMS in accordance with an embodiment of the present invention, having a system controller and a temperature varying GC column.

Referring first to FIG. 3a, a highly schematic arrangement of a sample preparation section of an EA-IRMS in accordance with an embodiment of the present invention is shown. Those components common to FIGS. 1a and 3a are labelled with like reference numerals.

Figure 1A:
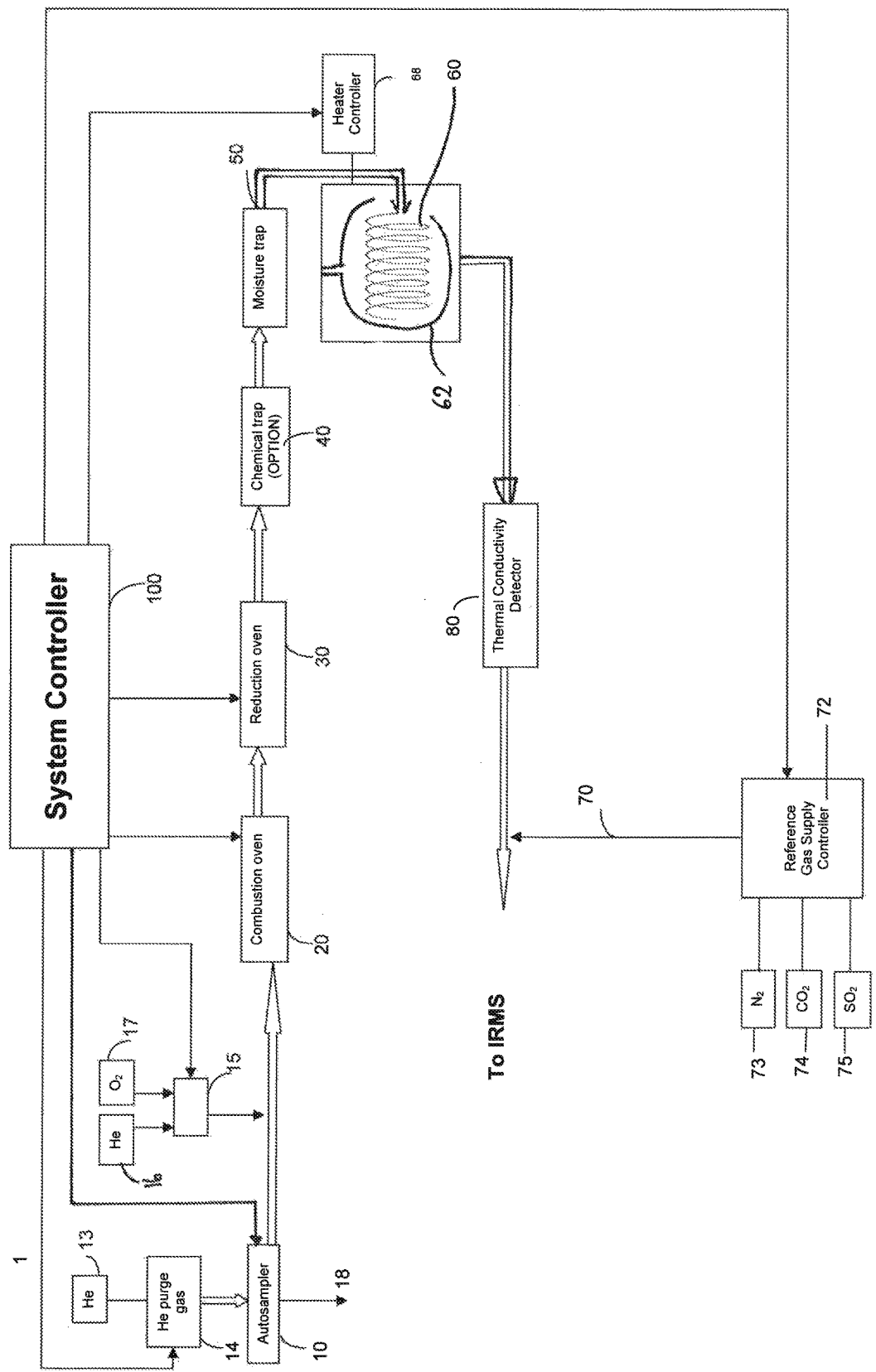
FIG. 1a shows a highly schematic arrangement of a part of a prior art elemental analysis isotope ratio mass spectrometer (EA-IRMS)
Figure 2:
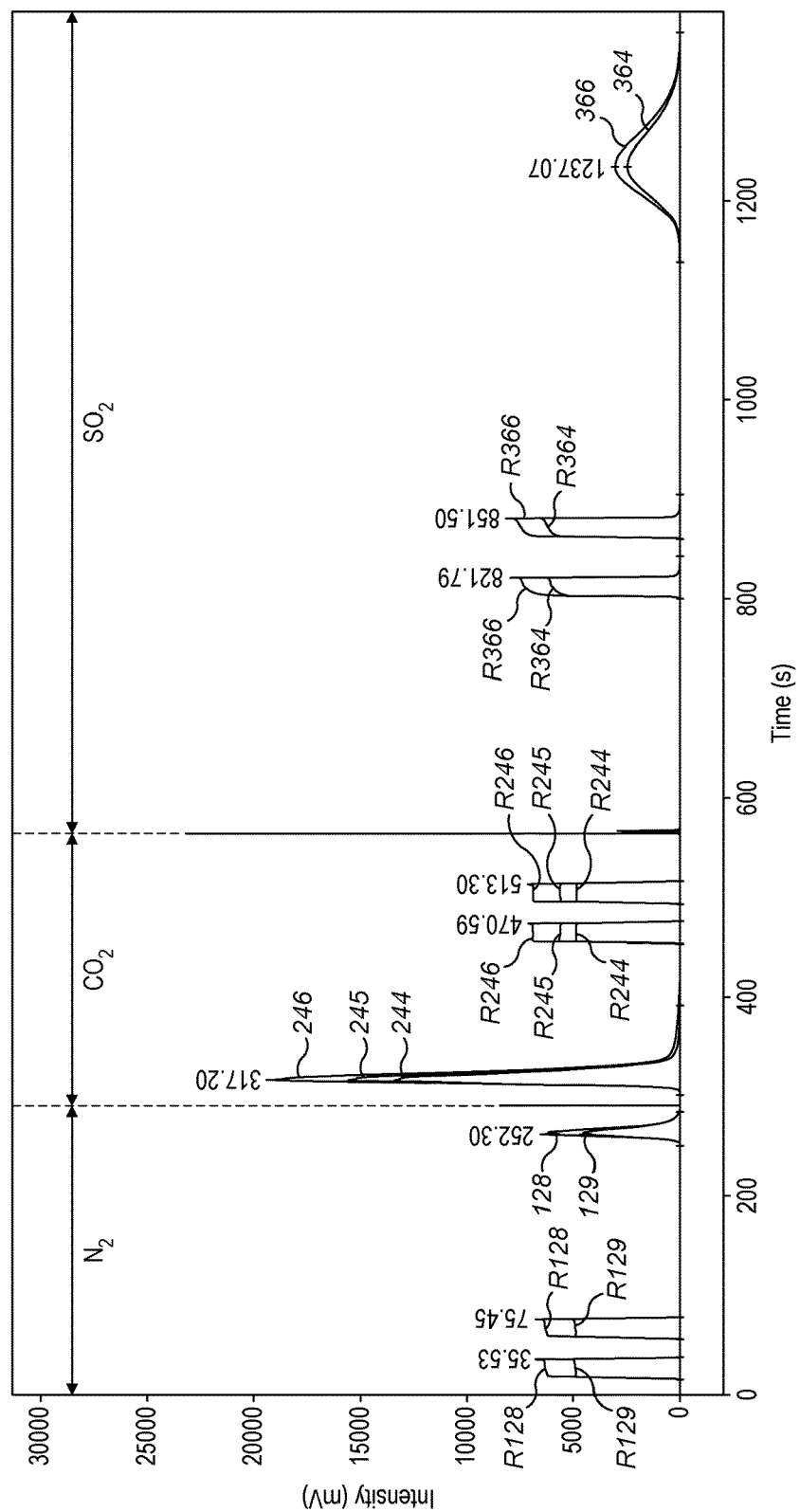
FIG. 2 shows a plot of the detected output of the EA-IRMS of FIG. 1a, during simultaneous Nitrogen, Carbon and Sulphur (NCS) analysis of a sample of Sulfanilamide.

The sample preparation and combustion/reduction proceeds, in the embodiment of FIG. 3a, in the same manner as was described in the Background section above, in respect of FIG. 1a. To avoid unnecessary repetition, this part of the process will only be summarised here.

A sample (not shown in FIG. 3a) is weighed and placed in a combustible capsule that is sealed and placed into an autosampler carousel 10 positioned above a combustion furnace 20. The autosampler carousel 10 injects the sealed sample capsule into the combustion furnace 20 under the control of a system controller 200. As before, Helium may be supplied to the autosampler 10 as a purge gas, and combustion in the combustion furnace 20 may be carried out in the presence of pulsed oxygen.

Helium carrier gas is employed to carry the sample across an oxygen donor compound. The flow rate of the helium carrier gas is again optimally between 40 and 200 mL/min, but can be up to 1000 mL/min. The reaction zone in the combustion furnace 20 is typically held at a temperature between 400 and 1100 degrees Celsius, with an ideal range of between 900 and 1050 degrees Celsius.

The resulting $NO_x$, $CO_2$, $SO_2$ and/or $H_2O$ products are reduced in a reduction oven 30, which may be a separate component as shown schematically in FIG. 3a, or may form a part of a single, combined combustion/reaction unit.

The reduction oven 30 is generally held at a temperature between 450-900° C. and the gases exiting that reduction oven are then directed through optionally a chemical trap 40 and a moisture trap 50, again as previously described; the order of the chemical and moisture traps 40, 50 may be reversed depending upon the reagents employed in each.

The dried gaseous output of the moisture trap 50 is introduced into a GC column 60, for separation of the gases. The GC column 60 of preferred embodiments of the present invention will be described in further detail below, but in general terms, the GC column 60 may preferably incorporate a carbon molecular sieve.

The GC column 60 of FIG. 3a is mounted within a GC chamber 250 whose interior is heated by halogen lamps 65. The halogen lamps 65 are controlled by a heater controller 68 which is connected to the system controller 200. A fan 240 draws ambient (cool) air into the interior of the chamber 250.

Figure 3B:
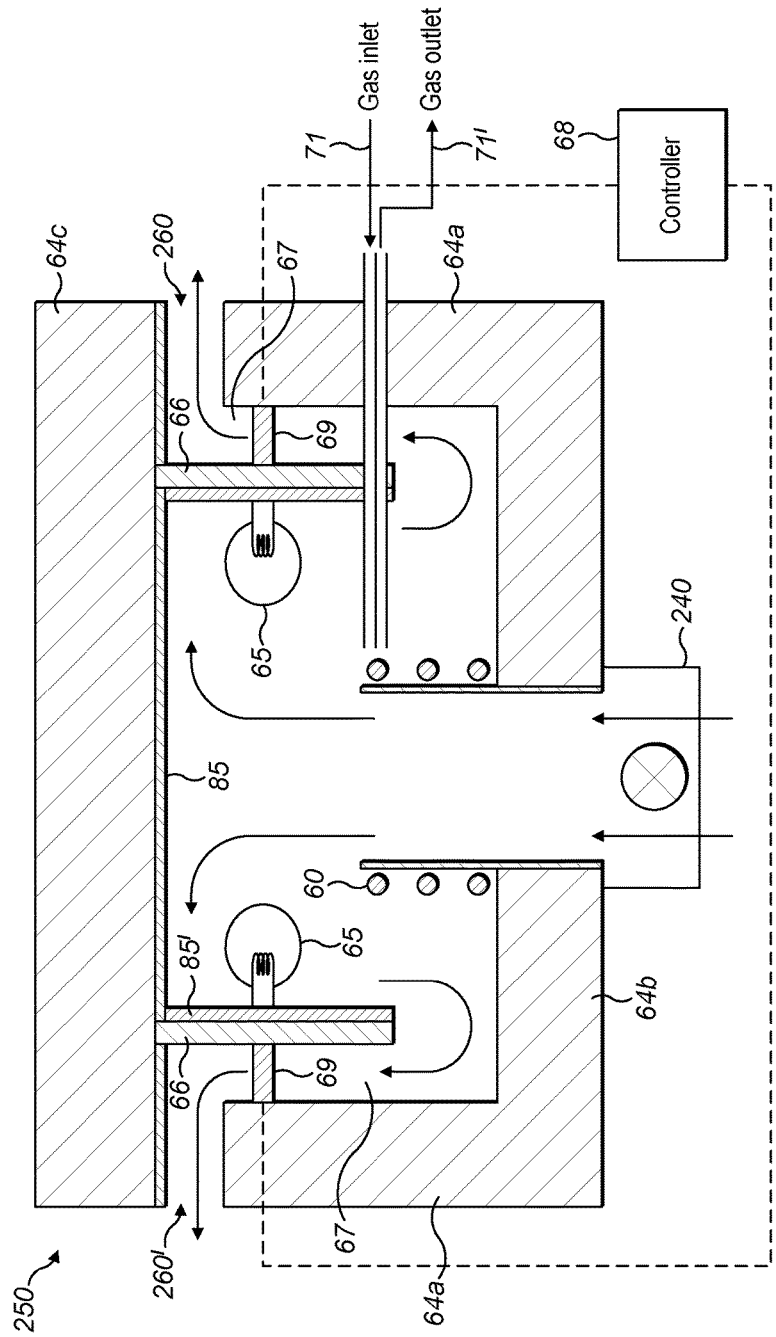

FIG. 3b shows an embodiment of the GC chamber 250 of FIG. 3a, in schematic sectional view. The GC chamber 250 contains the GC column 60 which is positioned generally centrally of the GC chamber 250. The GC chamber 250 has outer side walls 64a, a base 64b and a closure 64c, each of which are formed of an insulating material. The inner surfaces of the outer side walls 64a and the closure 64c have a reflective coating. The outer side walls 64a are separated from the closure 64c by openings 260, 260'.

Extending in an axial direction of the GC chamber 250 are inner walls 66. The inner walls are also coated or formed from a reflective material. The inner walls 66 are spaced inwardly of the outer side walls 64a of the GC chamber 250 so as to define fluid channels 67 which communicate with a central region of the GC chamber at a first end proximal the GC column 60 and the base 64b, and which communicate with the openings 260, 260' at a second end. The halogen lamps 65 are mounted outwardly of the GC column 60, upon the inner walls 66, so that, in use, heat is radiated from the halogen lamps 65 towards the GC column 60. Electrical power is supplied from the exterior of the GC chamber 250 to the halogen lamps 65 via electrical standoffs 69 extending outwardly across the fluid channels 67. A gas supply inlet 71 and a gas outlet 71' are also provided which extends outwardly through the outer side walls 64a to the GC column 60 so that the sample and/or reference gases generated upstream of the GC column 60 (FIG. 3a again) can be introduced into the GC column 60 and leave the GC column 60 as gaseous output.

The fan 240 is, as noted above in connection with FIG. 3a, mounted externally of the GC chamber 250 and, in use, draws ambient (relatively cool) air from outside of the GC chamber 250 and blows it into the central part of the GC chamber 250. The relatively cool air forces any relatively warm or hot air present in the vicinity of the GC column 60 to be expelled from the GC chamber 250 along the fluid channels 67 and out via the openings 260, 260'.

Rapid ramping up (heating) and down (cooling) of the temperature of the GC column 60 can thus be achieved. To achieve rapid heating, the system controller 200 sends a trigger signal to the heater controller 68 which applies electrical power to the halogen lamps in order to cause the temperature in the GC chamber 250 to be increased. The heater controller 68 may be programmed with one or many temperature profiles (some examples of which will be described in respect of later Figures) that cause the temperature of the GC column 60 to be ramped up to one or more temperature set points. The skilled person will recognise that proportional-integral-differential (PID) or other known feedback control techniques may be employed in order that the set point temperatures are reached without excessive overshoot or oscillations.

The temperature may be ramped between first and second set points at a constant (or substantially constant) rate. The heater controller 68 may be configured to ramp between different set point temperatures at different constant rates, depending for example upon the experiment being carried out and the constituent compounds, molecules etc. Additionally or alternatively, the rate of temperature change between two set points may be non-linear, or may be linear over a part of the time and non linear at other times. It is moreover to be understood that the temperature gradient does not even need to be constantly positive between the two set points, provided only that, during elution of gases through the GC column, there is a net positive increase in temperature.

For example, it appears that providing a small temperature change even at the start of the experiment, when the GC column 60 is eluting the $N_2$ and $CO_2$, can improve further the baseline separation. So the temperature ramp could start slowly and then increase in rate as the temperature of the GC column 60 rises.

The arrangement described above in connection with FIG. 3b also allows rapid cooling of the GC column 60 between experiments. In particular the fan 240 and the arrangement of the outer side walls 64a and the inner walls 66, resulting in the fluid channels 67, allows the cool air blown by the fan 240 to rapidly purge the GC chamber 250 of warm or hot air in order to allow a lower starting set point temperature to be rapidly attained.

Separated gases eluting from the GC column 60 are then conveyed through a thermal conductivity detector (TCD) 80 for weight percent measurements. After (non destructive) analysis by the TCD 80, the analyte gases are directed into an isotope ratio mass spectrometer for simultaneous measurement of $\delta^{13}C$, $\delta^{15}N$ and $\delta^{34}S$ values.

In the IRMS (not shown in FIG. 3a), the combusted, reduced gases are ionized and passed through a magnetic sector analyser where they separate in space according to their mass to charge ratios. The resulting spatially separated ion species are detected at a plurality of Faraday detectors in a detector array.

Techniques for ionization, separation and detection in the IRMS will be familiar to the skilled reader. The details of the IRMS do not in any event form a part of the present invention and will not be discussed further.

Figure 4:
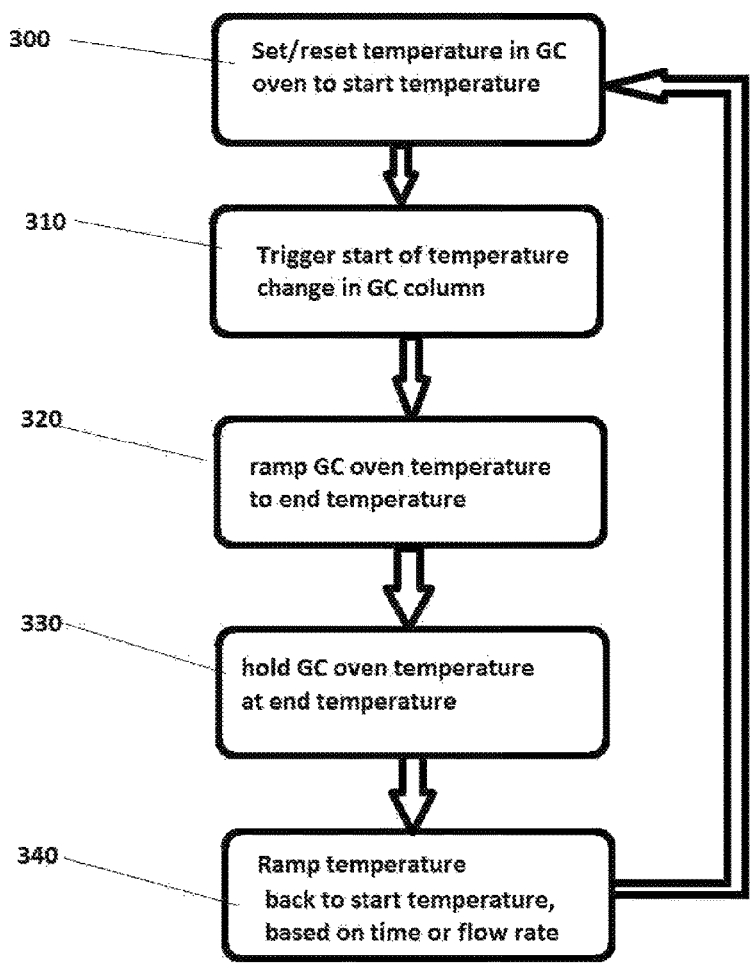
FIG. 4 shows a flowchart illustrating the operation of the system controller and GC column of FIGS. 3a and 3b using a temperature increase during sample analysis.

Turning now to FIG. 4, a flow chart illustrating the steps carried out during Gas Chromatography is shown. At step 300, the system controller 200 sends a set/reset signal to the heater controller 68 of the halogen lamps 65 to hold or move the temperature measured at the GC column 60 to a start temperature $T_{start}$. The start temperature $T_{start}$ of the GC column 60 is held between 45 and 80 degrees Celsius, but is ideally in the range of 50 to 70 degrees Celsius. In a most preferred embodiment, the system controller 200 sends a set/reset signal to the heater controller 68 so that the GC column 60 is held at 50 degrees Celsius for $N_2$ and $CO_2$ separation.

Once the temperature of the GC column 60 is stabilized at the desired start temperature $T_{start}$, a ramp up trigger signal is generated. This ramp up trigger signal may be generated based upon a predetermined time—for example, the ramp up trigger signal may be generated at a time $t_5$ after the system controller has instructed the autosampler 10 to inject the sample billet into the combustion oven 20. The time $t_5$ may itself be predetermined through factory or user calibration or may be user settable. Alternatively, the ramp up trigger signal may be generated based upon detection of a threshold gas flow rate of $N_2/CO_2$ at the GC column 220 and/or the GC chamber entrance, for example.

At step 310 of FIG. 4, the heater controller 68 receives the ramp up trigger signal from the system controller 200 and commences a temperature ramp (step 320). In the preferred embodiment, this results in a rapid rise in the temperature of the GC column 60 from the start temperature $T_{start}$ (preferably 50 degrees Celsius) to an end temperature $T_{end}$, which is (again in the preferred case) 150 degrees Celsius. By "rapid rise" is meant a change from $T_{start}$ to $T_{end}$ over several tens of seconds, and most preferably over 1 to 3 minutes.

As noted above, the heater controller 68 controls the temperature of the GC column 60 so as to ramp up at a linear rate, a non linear rate, or a combination of the two.

At step 330, once one or more temperature sensors in the GC chamber 250/GC column 60 (not shown in FIG. 3a or 3b) determine that the end temperature $T_{end}$ has been reached, the heater controller 68 of the halogen lamps 65 then controls the temperature of the GC column 60, so that the temperature of the GC column 60 is held constant at the temperature $T_{end}$. The time over which the GC column 60 is held at temperature $T_{end}$ may, as with $T_{start}$, either be pre-programmed within the heater controller 68 based upon factory or user calibration, or may be user selected, or may be based upon detection of a threshold of gas flow. As was explained in the Background section, $SO_2$ elutes more slowly than $N_2$ and $CO_2$ so the system controller 200 may look for a threshold of $SO_2$ gas flow into the GC column 60 for example.

Once system controller 200 determines, based on a time, a user input or a threshold gas flow rate, that the GC column temperature is to be reset, a ramp down trigger signal is generated by the system controller 200 and sent to the controller 68 of the halogen lamps 65. This results in a rapid cooling of the GC column 60: see step 340 of FIG. 4. The temperature drop is (as with the temperature rise) typically tens of seconds and optimally 2 minutes. As explained in connection with FIGS. 3*a* and 3*b* above, rapid cooling is preferably facilitated by the use of the fan 240 which blows cool air into the GC chamber 250 in order to displace warm or hot air adjacent the GC column 60 The final temperature following ramp down is $T_{start}$ again.

Once the temperature has reached $T_{start}$, the control loop reverts to step 300 again, ready for a next sample to be loaded into the EA-IRMS by the autosampler 10.

FIGS. 5, 7, 8 and 10 show chromatograms measured with EA-IRMS. For the sake of clarity, reference peaks are not shown in those chromatograms, and only the peaks of the isotope of the molecules having the highest abundance ($N_2$: isotope mass 28 u, $CO_2$: isotope mass 44 u and isotope mass $SO_2$: 64 u) are shown.

Figure 5:
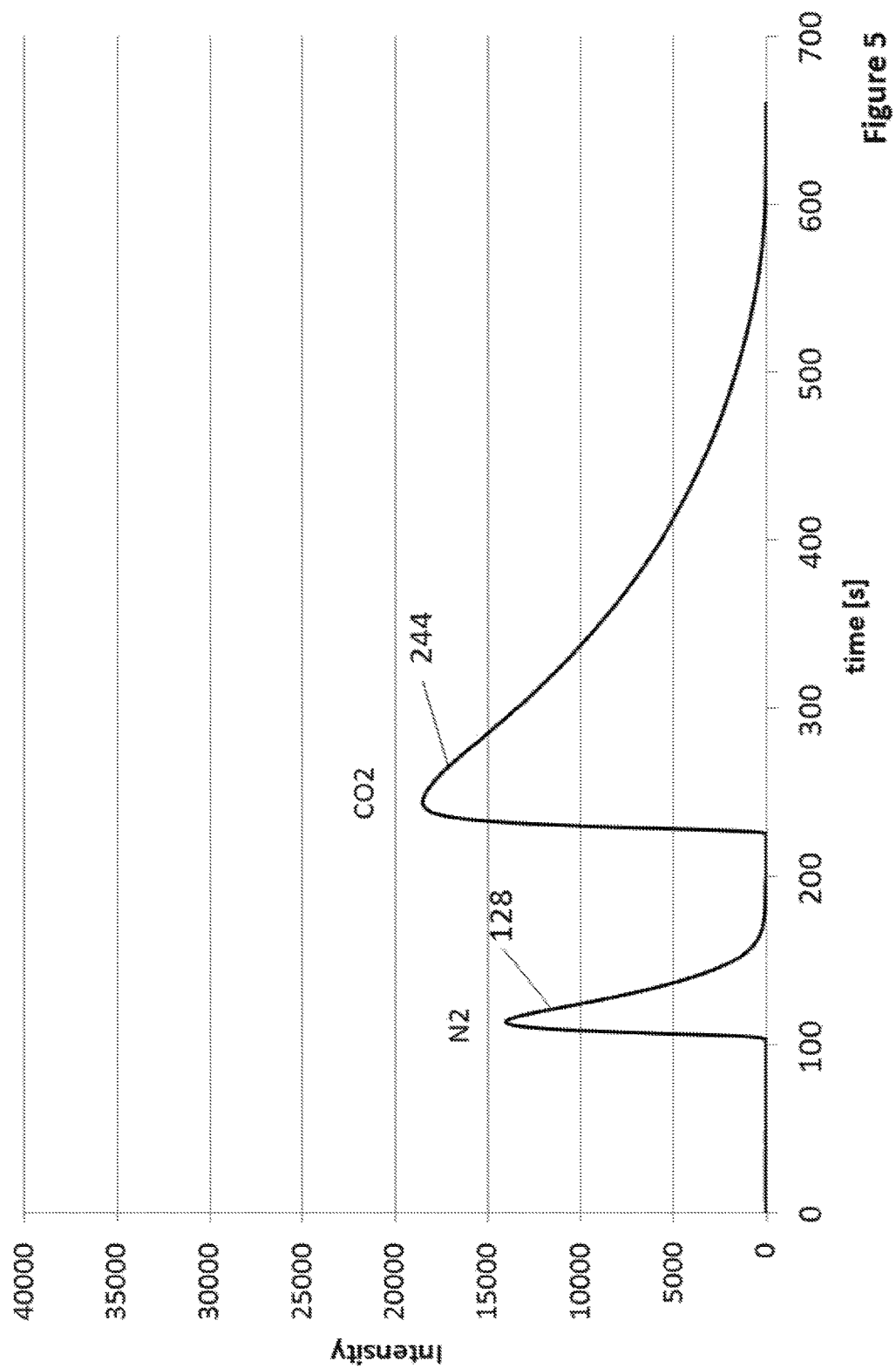
FIG. 5 shows a chromatogram of $N_2$ and $CO_2$ peaks obtained from a prior art EA-IRMS with an isothermal GC, using caffeine as a sample.

FIG. 5 shows a chromatogram of $N_2$ and $CO_2$ peaks obtained from a prior art EA-IRMS with an isothermal GC column, using caffeine as a sample. The left hand peak 100 in FIG. 5 arises from $N_2$, whilst the right hand peak 200 is derived from $CO_2$ Peak tailing is apparent in FIG. 5.

Figure 6:
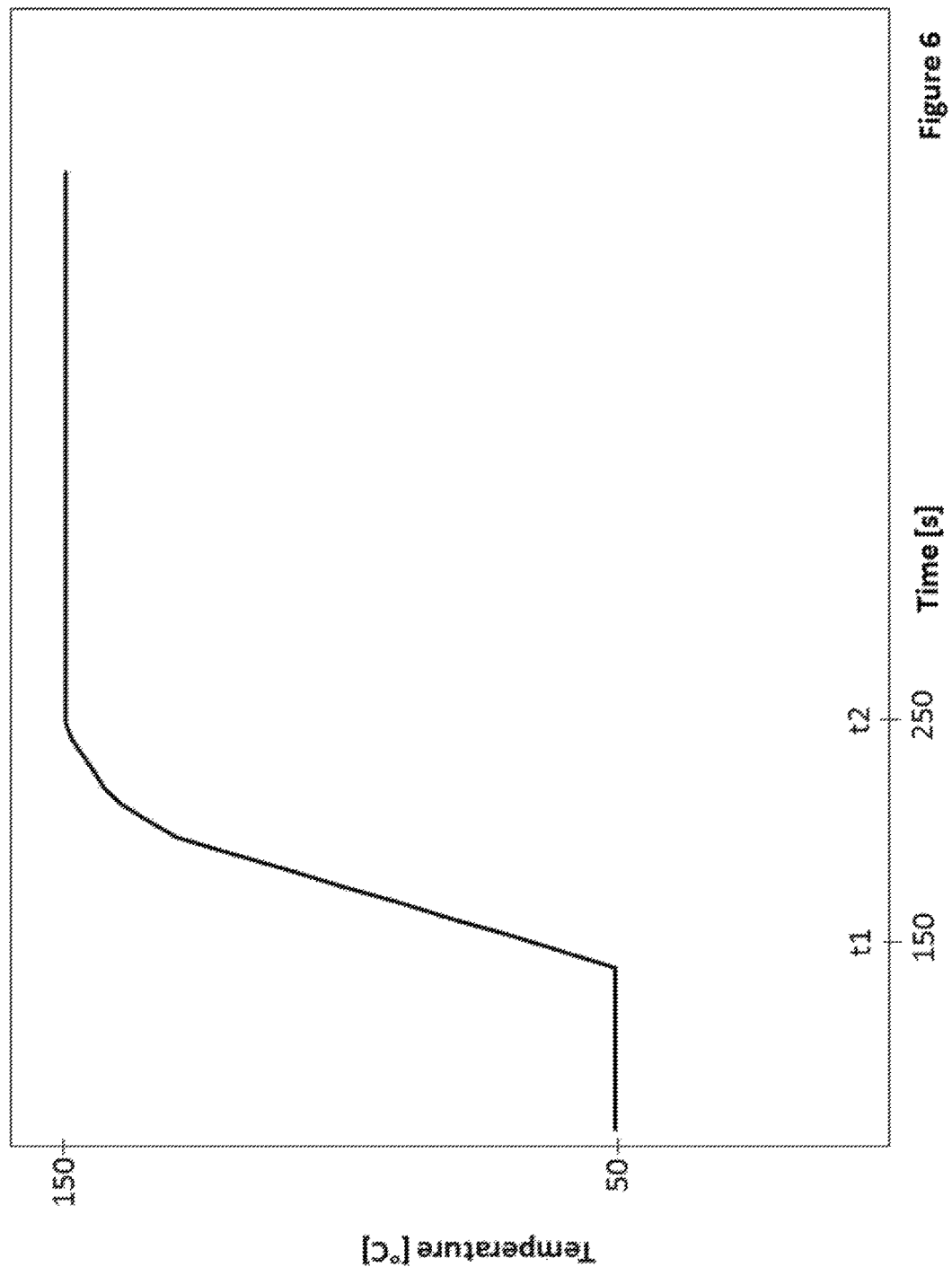
Figure 7:
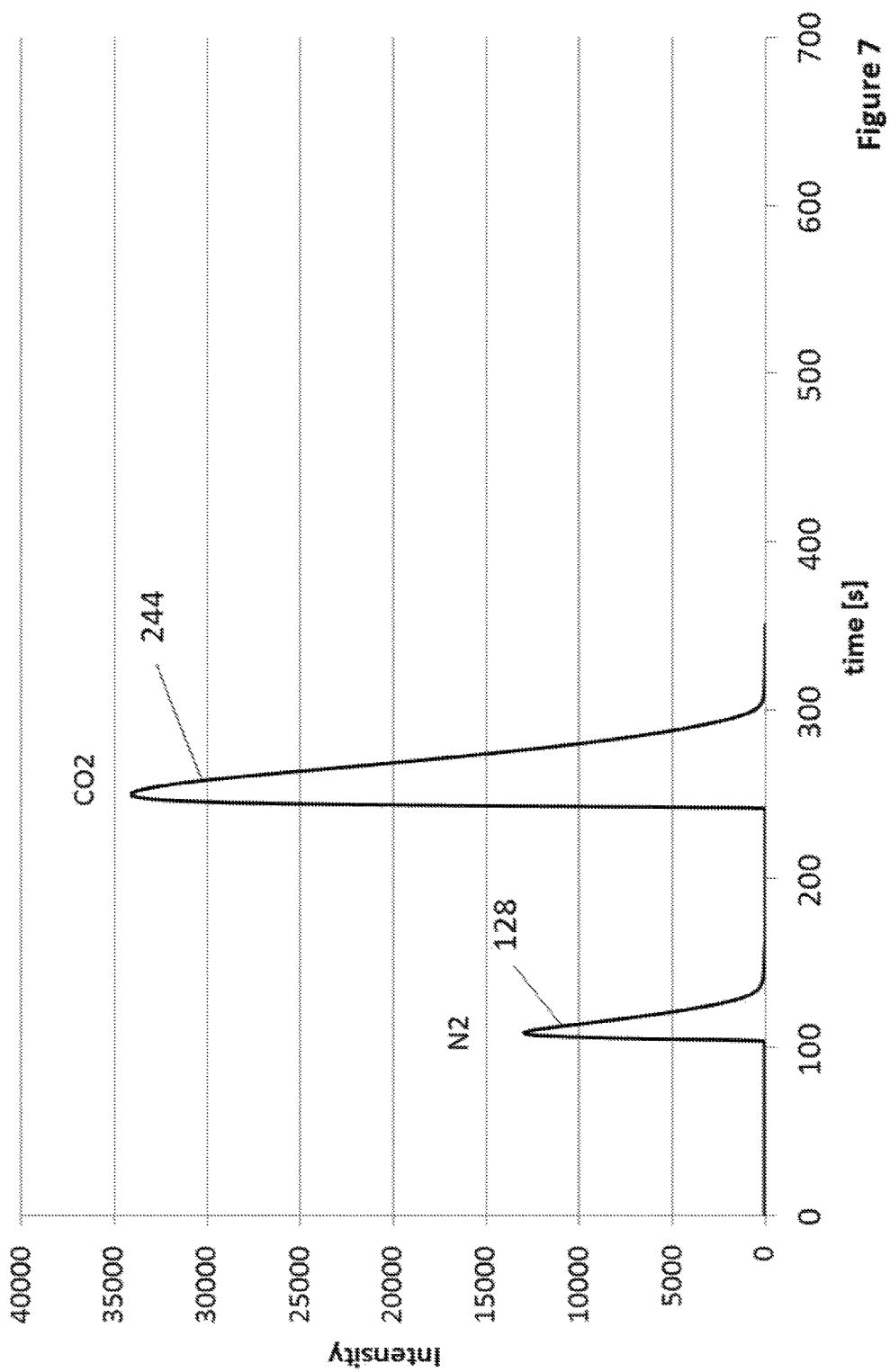
FIG. 7 shows a chromatogram of $N_2$ and $CO_2$ peaks obtained from an EA-IRMS embodying the present invention, to which the temperature profile of FIG. 6 is applied during sample elution, again using caffeine as a sample.

FIG. 6 shows a first exemplary temperature profile that may be applied to the temperature variable GC column 60 of FIGS. 3*a* and 3*b*. The temperature profile of FIG. 6 is, in particular, applied to the GC column 60 by the heater controller 68 based upon a trigger signal from the system controller 200. It will be seen that the start temperature $T_{start}$ is 50 degrees Celsius and the heater controller 68 holds the GC column 60 at that temperature for 150 seconds. At that point, the heater controller 68 causes the power supplied to the halogen lamps 65 to be increased so that the GC column temperature rises in a linear manner from 50 up to 150 degrees Celsius over a period of 100 seconds. The heater controller 68 then maintains the GC column 60 at the upper set temperature $T_{end}$ of 150 degrees Celsius until the experiment is concluded. The temperature is then ramped back down again but this is not shown in FIG. 6. FIG. 7 shows a chromatogram of $N_2$ and $CO_2$ peaks obtained from the EA-IRMS embodying the present invention, such as is shown in FIGS. 3*a* and 3*b*, to which the temperature profile of FIG. 6 is applied during sample elution, again using caffeine as a sample. It will be seen that the $N_2$ peak 128 and the $CO_2$ peak 244 are each much narrower than in FIG. 5, with the peak tailing much reduced. The separation between the two peaks 128, 244 is thus greatly increased.

The GC column employed to generate the chromatograms of FIGS. 5 and 7 contains a porous material. The pore mean diameter of the porous material is preferably larger than 50 Angstrom, particularly preferably larger than 65 Angstrom, and in the specific embodiment employed to obtain the chromatograms of FIGS. 5 and 7, is 70 Angstrom (1 Angstrom=$1*10^{-10}$ m).

The material in the GC column has a a large surface area (preferably larger than 900 $m^2/g$, particularly preferably larger than 1100 $m^2/g$.) Again in the embodiment employed to obtain the chromatograms of FIGS. 5 and 7, the material in the GC column has a surface area of larger than 1100 $m^2/g$.

The GC column can be filled with spherical carbon. The GC column employed to obtain the chromatograms of FIGS. 5 and 7 is filled with a spherical carbon molecular sieve.

The GC column is preferably filled with a spherical material having a diameter between 0.12 mm and 0.5 mm, preferably between 0.15 mm and 0.4 mm and particularly preferably between 0.2 mm and 0.35 mm. The GC column employed to generate the chromatograms of FIGS. 5 and 7 is filled with a spherical material having a diameter between 0.2 mm and 0.4 mm.

Figure 8:
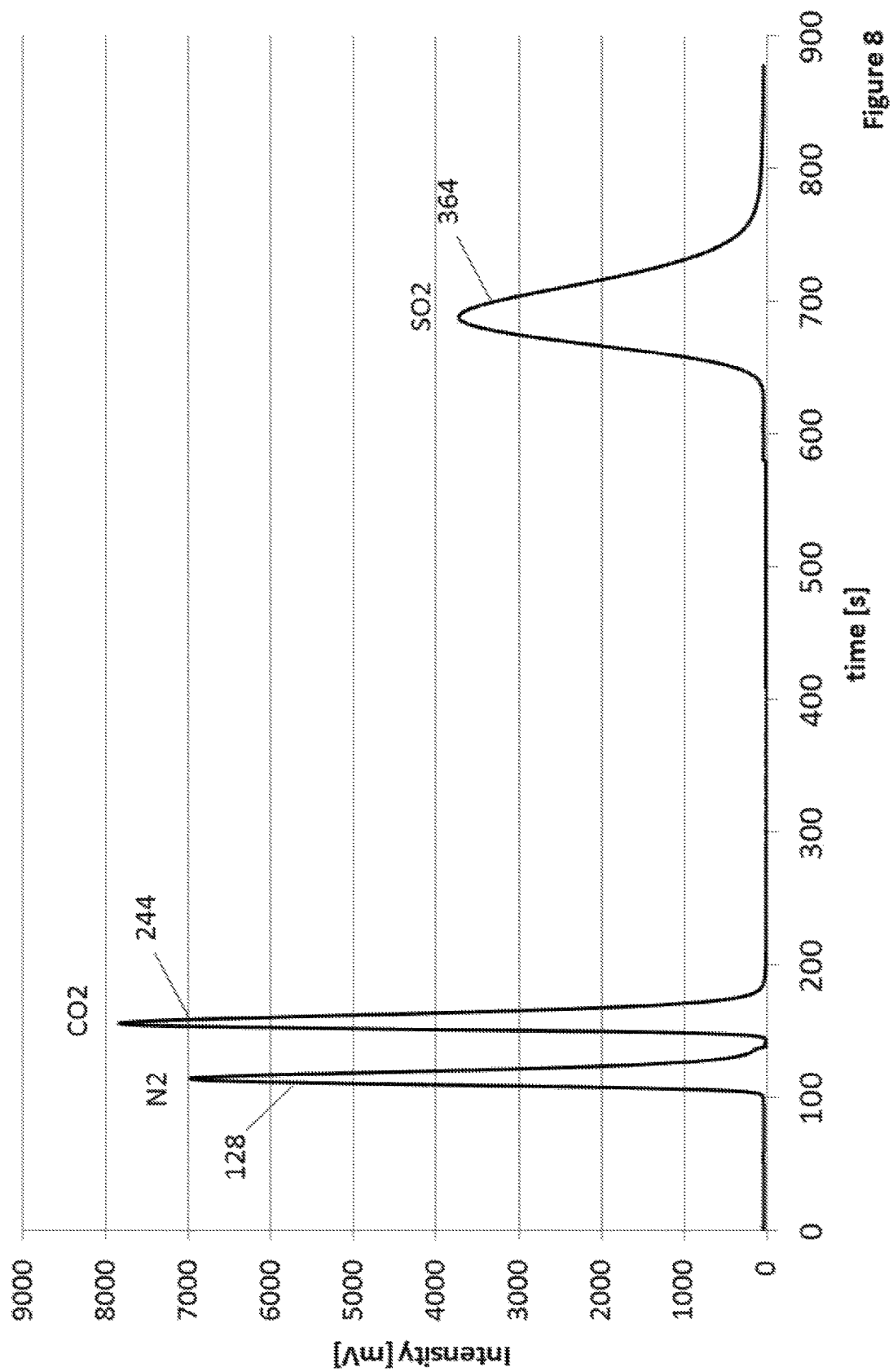
FIG. 8 shows a chromatogram of $N_2$, $CO_2$ and $SO_2$ peaks obtained from a prior art EA-IRMS with an isothermal GC, using sulfanilamide as a sample.

FIG. 8 shows a chromatogram of $N_2$, $CO_2$ and $SO_2$ peaks obtained from a prior art EA-IRMS with an isothermal GC, using sulfanilamide as a sample. The $N_2$, and $CO_2$ peaks 128, 244 in FIG. 8 are close together and again exhibit peak tailing; the tail of the $N_2$ peak 128 runs into the leading edge of the $CO_2$ peak 244. The $SO_2$ peak 364 is broad with a FWHM (full width of half maximum) of around 60 seconds.

Figure 9:
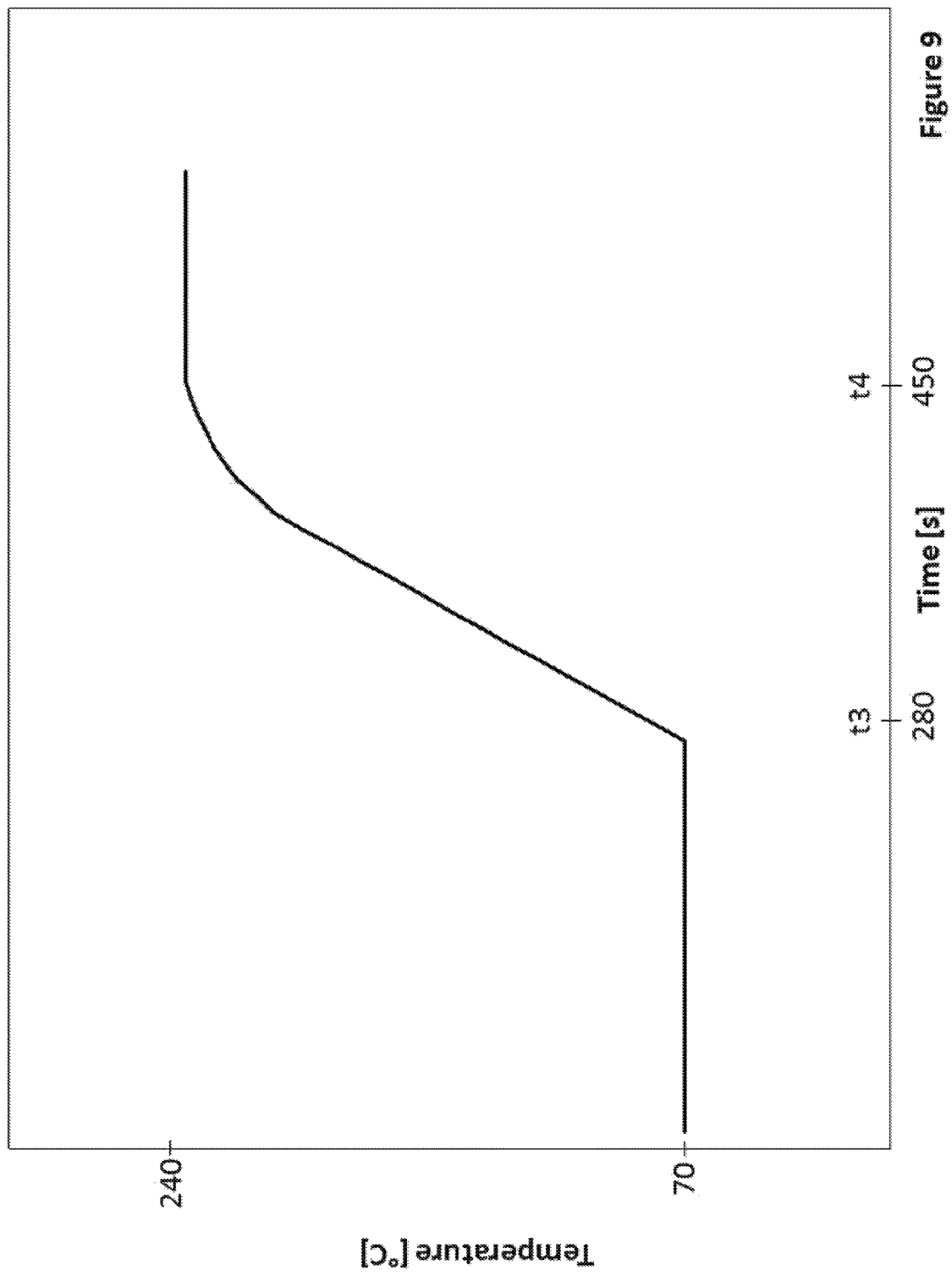

FIG. 9 shows a second exemplary temperature profile that may be applied to the temperature variable GC column 60 of FIGS. 3*a* and 3*b*. The temperature profile of FIG. 9 is, in particular, applied to the GC column 60 by the heater controller 68 based upon a trigger signal from the system controller 200. It will be seen that the start temperature $T_{start}$ in the profile of FIG. 9 is 70 degrees Celsius and the heater controller 68 holds the GC column 60 at that temperature for 280 seconds. At that point, the heater controller 68 causes the power supplied to the halogen lamps 65 to be increased so that the GC column temperature rises in a linear manner from 70 up to 240 degrees Celsius over a period of 170 seconds. The heater controller 68 then maintains the GC column 60 at the upper set temperature $T_{end}$ of 240 degrees Celsius until the experiment is concluded. The temperature is then ramped back down again but this is not shown in FIG. 9. The benefit of this heat and cool strategy is based upon the strongly differing elution speeds of $N_2$ and $CO_2$ on the one hand, and $SO_2$ on the other. As the three gases arrive at the GC column 60 with the latter held at $T_{start}$ (70 degrees Celsius for example), the $SO_2$ is relatively slowly eluting over the column. Once the temperature is ramped up to $T_{stop}$, the $SO_2$ experiences a higher temperature and this reduces the $SO_2$ elution time.

Reduction in the $SO_2$ elution time causes the peak in the resulting mass spectrum to be sharper and with minimal tailing. This beneficial effect is clearly seen in FIG. 10, which shows EA-IRMS analysis of the same sample (sulfanilamide) as was employed to generate the prior art isothermal mass spectrum of FIG. 8. Comparing FIGS. 8 and 10, the $SO_2$ peak 364 at the right hand side of the chromatogram is seen to be much sharper. The temperature ramping scheme of FIG. 9 results in an $SO_2$ peak width (full width at half maximum) of around 25-30 seconds (time is shown on the horizontal axis). This is nearly half of the peak width shown in FIG. 8 that employs isothermal GC, where the broad flat peak (full width at half maximum) there is around 60 s wide.

Figure 10:
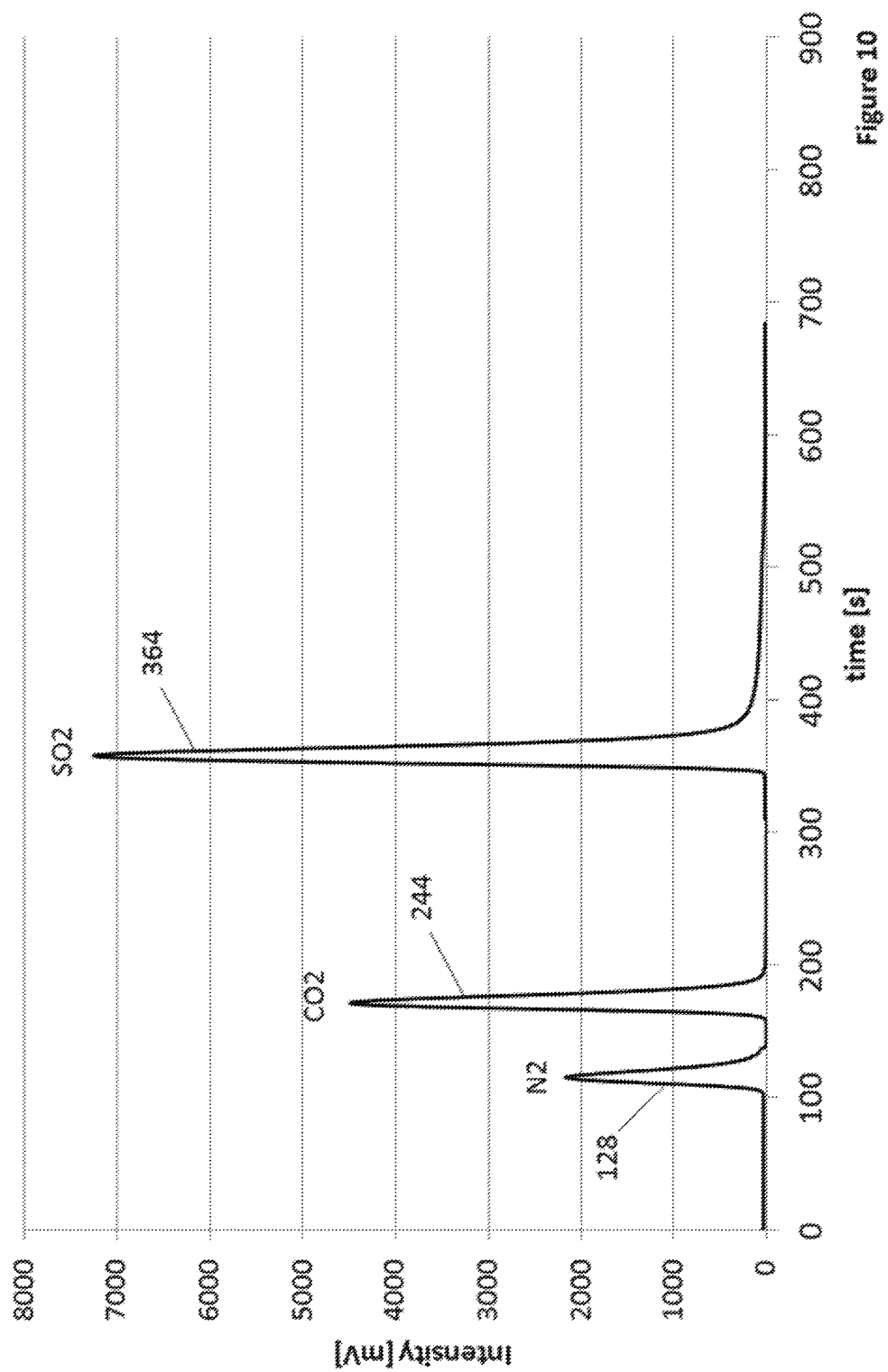
FIG. 10 shows a chromatogram of $N_2 CO_2$ and $SO_2$ peaks obtained from an EA-IRMS embodying the present invention, to which the temperature profile of FIG. 9 is applied during sample elution, again using sulfanilamide as a sample.

The GC column used to generate the chromatogram of FIGS. 8 and 10 contains a porous material, again preferably with large pores (eg pore mean diameter greater than 50

Angstroms). The column is filled with a material having a large surface area, eg at least 900 m²/g. The filler is a polymer having a spherical shape and a silanised surface. The column is filled with a spherical material preferably having a diameter between 0.12 mm and 0.5 mm and in the specific arrangement employed to generate the chromatogram of FIGS. 8 and 10, it is between 0.15 and 0.35 mm. Overall, the total analysis time employing the scheme described above is less than 12 minutes, and all peak integration is concluded in around 9-10 minutes. Thus there is at least a 33% improvement in analysis time when changing the temperature of the GC column 60 during an analysis, relative to the prior art isothermal GC analysis (where, as discussed in the Background section, compromise times of 18 minutes are employed). A reduction in sample analysis time improves sample throughput and system productivity.

A further benefit of the reduced analysis time is that the volume of Helium purge/carrier gas needed to complete each experiment can be reduced. A flow of helium gas only needs to be present during the sample analysis phase. At other times, the flow can be throttled. If the time taken to carry out each experiment can be reduced by a third, this offers the opportunity to save very significant amounts of helium over an extended period of use of the improved EA-IRMS device of the present invention. Reactor lifetime and chemical trap lifetime may also be extended when using a non-isothermal temperature profile, since the improved analytical and workflow procedures outlined above reduce the time per experiment, and provide an increased maintenance interval.

One further surprising consequence of the use of a non-isothermal temperature profile during EA-IRMS is that simultaneous $\delta^{13}C$, $\delta^{15}N$ and $\delta^{34}S$ measurements, along with % C, % N and % S measurements, are achievable even for those bulk organic samples such as wood or bone collagen, where the ratio of Carbon to Sulphur can exceed 5000:1, preferably 7000:1 and particularly preferably 10,000:1. As a result, it is often not necessary to repeat an experiment multiple times (in order to obtain a statistically acceptable result), as can often be the case with isothermal GC analyses.

Figure 11:
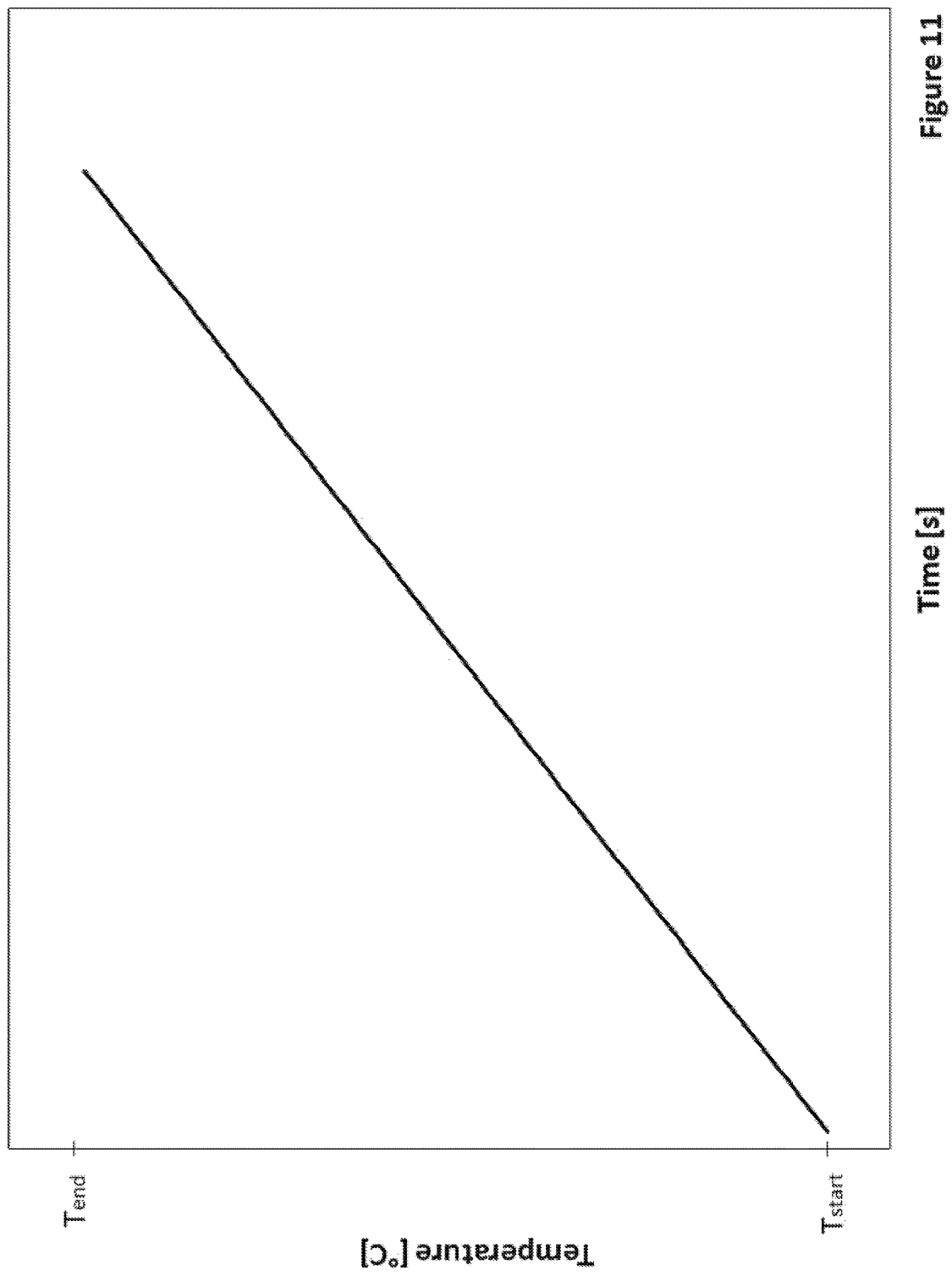
FIG. 11 shows a third exemplary temperature profile that may be applied to the temperature varying GC column of the invention.
Figure 12:
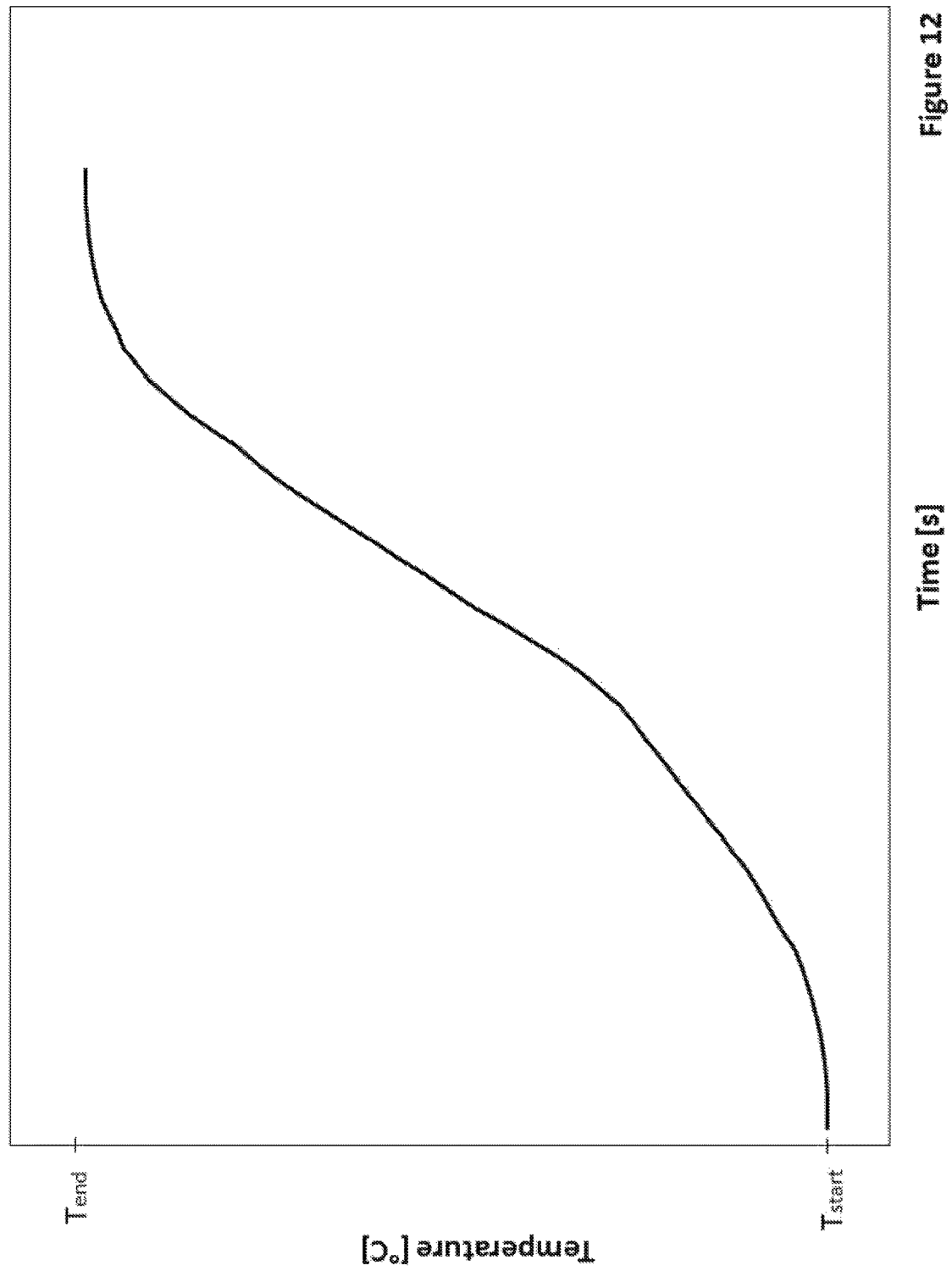
FIG. 12 shows a fourth exemplary temperature profile that may be applied to the temperature varying GC column of the invention.

Turning now to FIGS. 11-17, various different exemplary temperature ramping schemes are shown. In FIG. 11, the temperature gradient is constant (ie the slope is linear). In FIG. 12, the temperature gradient is non linear between the start and finish temperature, and in particular the rate of change of temperature is relatively low at the start and finish of the temperature ramping, reaching a maximum around half way between $T_{start}$ and $T_{end}$.

Figure 13:
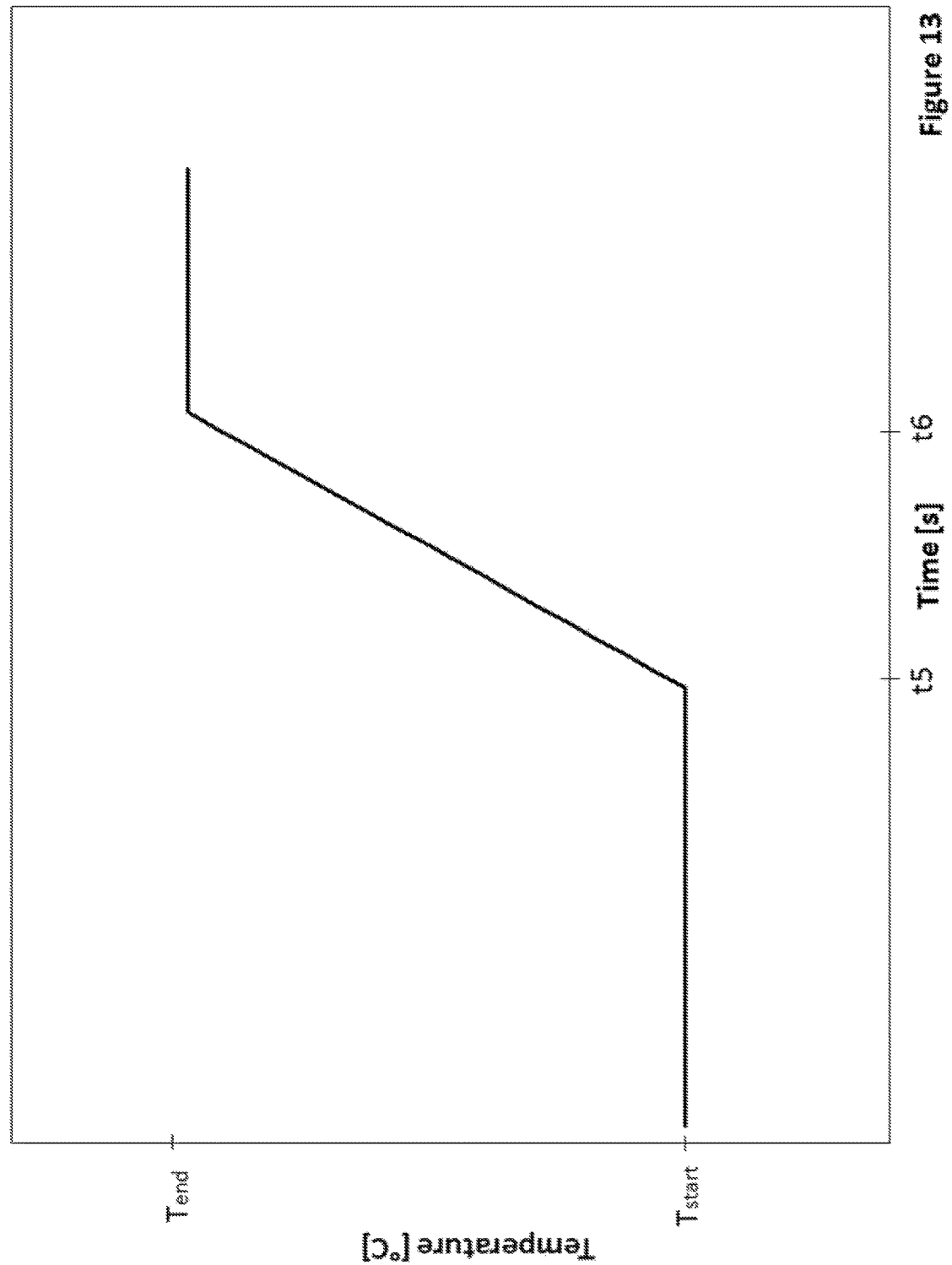
FIG. 13 shows a fifth exemplary temperature profile that may be applied to the temperature varying GC column of the invention.
Figure 14:
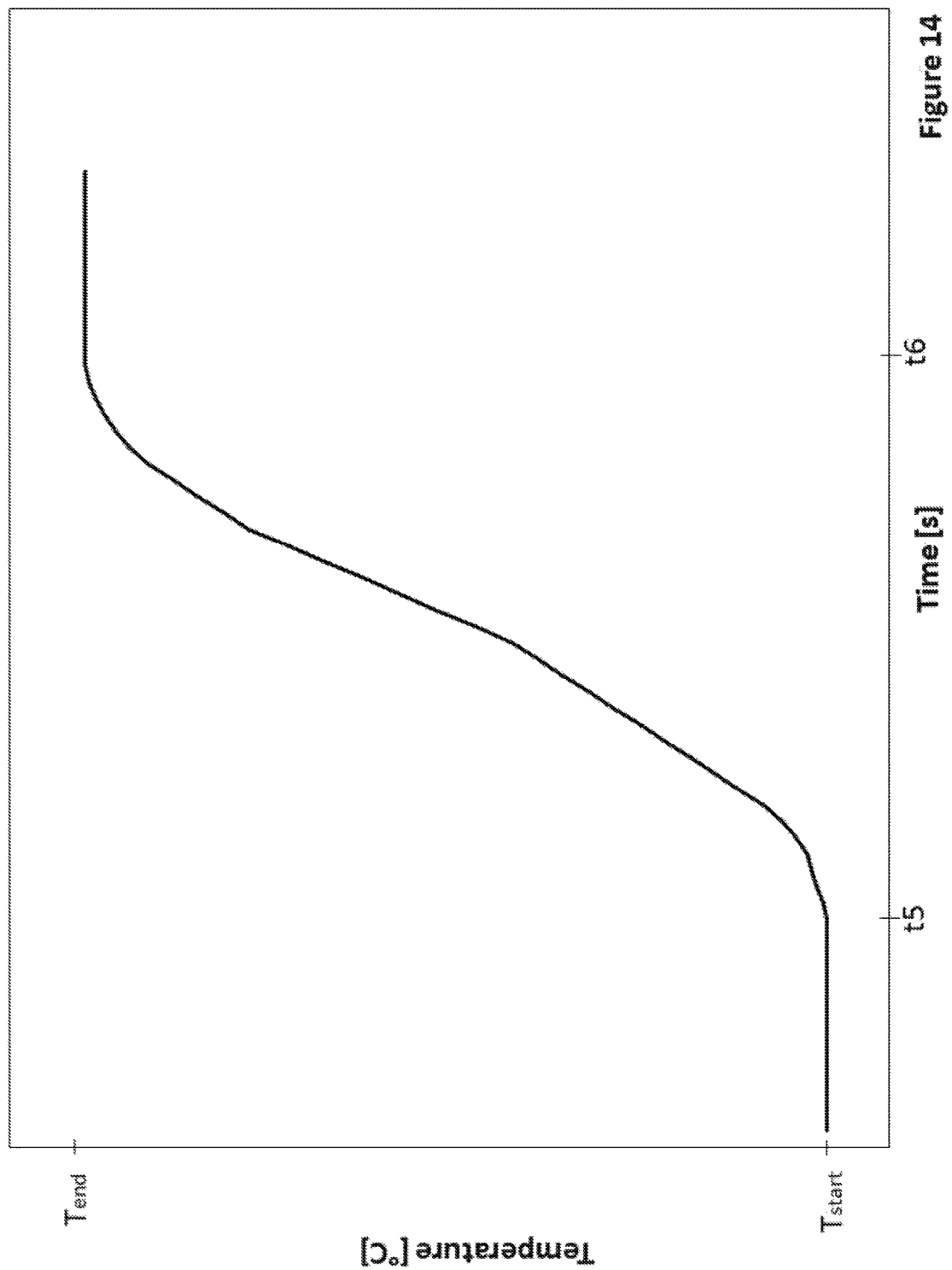
FIG. 14 shows a sixth exemplary temperature profile that may be applied to the temperature varying GC column of the invention.

FIG. 13 illustrates the use of two plateaus with a linear gradient between the two. FIG. 14 by contrast employs a non-linear gradient between two plateaus, again with the rate of change of temperature being slowest towards the start and end temperatures $T_{start}$ and $T_{end}$, and with the most rapid change being between those two temperatures.

Figure 15:
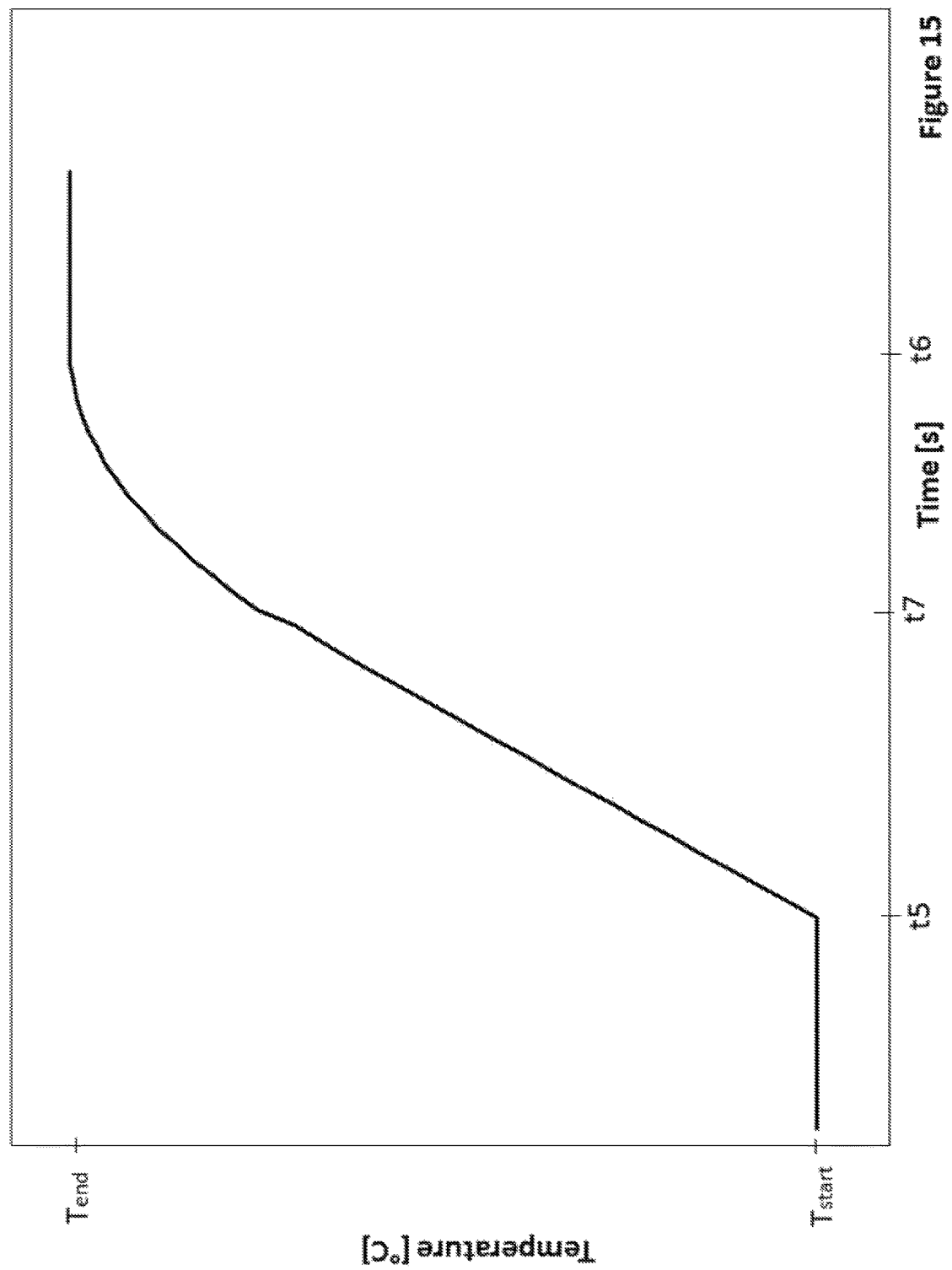
FIG. 15 shows a seventh exemplary temperature profile that may be applied to the temperature varying GC column of the invention.

FIG. 15 employs two plateaus again, but this time has zero gradient at the start temperature $T_{start}$ up to $t_5$ (to form the first plateau), a constant gradient between $t_5$ and $t_7$, then a non constant gradient between $t_7$ and $t_6$ and finally a zero gradient after $t_6$ at the end temperature $T_{end}$ (to form the second plateau).

Figure 16:
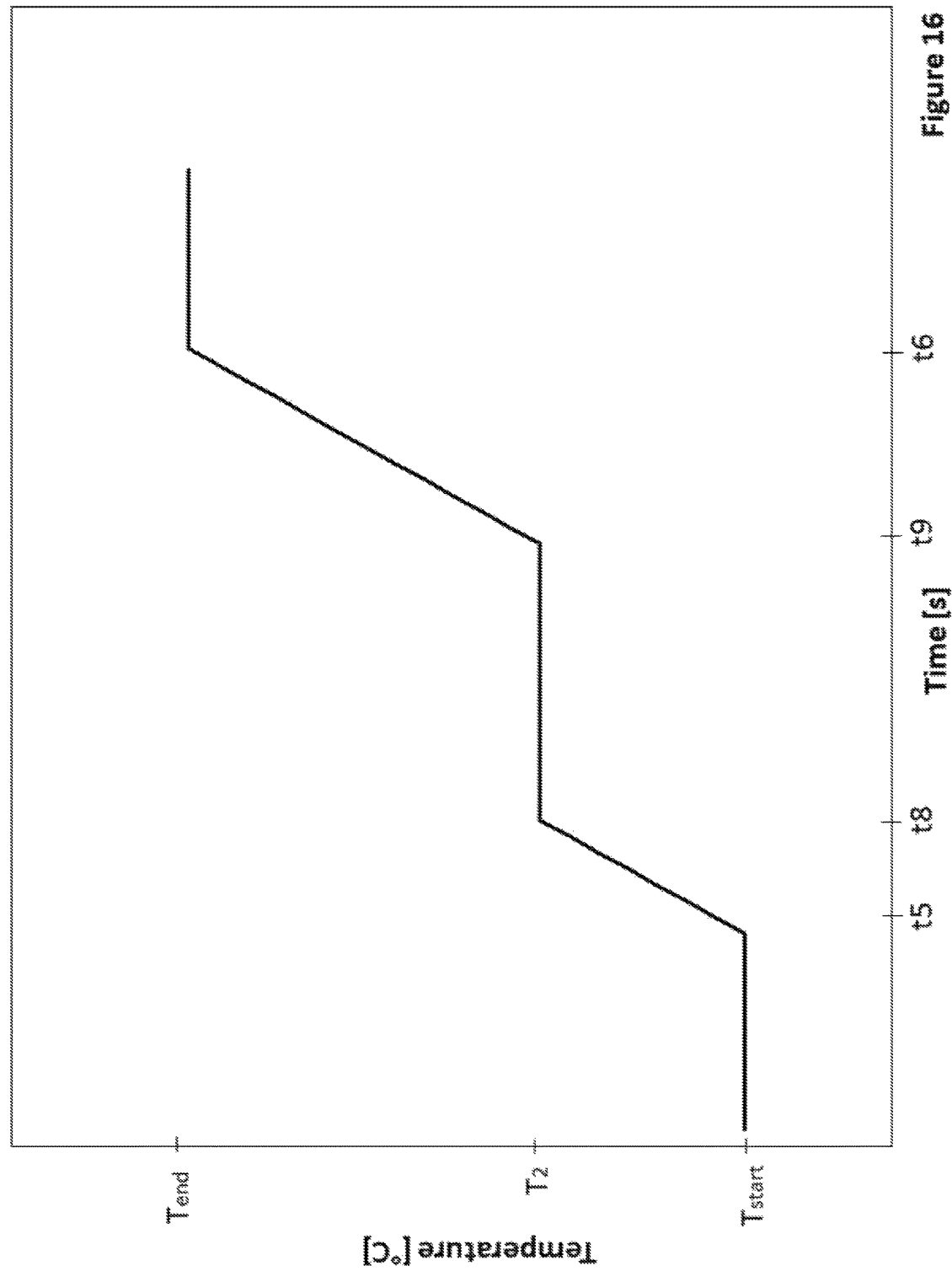
FIG. 16 shows an eighth exemplary temperature profile that may be applied to the temperature varying GC column of the invention.

FIG. 16 employs three plateaus rather than two, with a constant gradient between the first and second, and another constant gradient between the second and third plateaus (which may be the same as or different to the gradient between the first and second plateaus).

Figure 17:
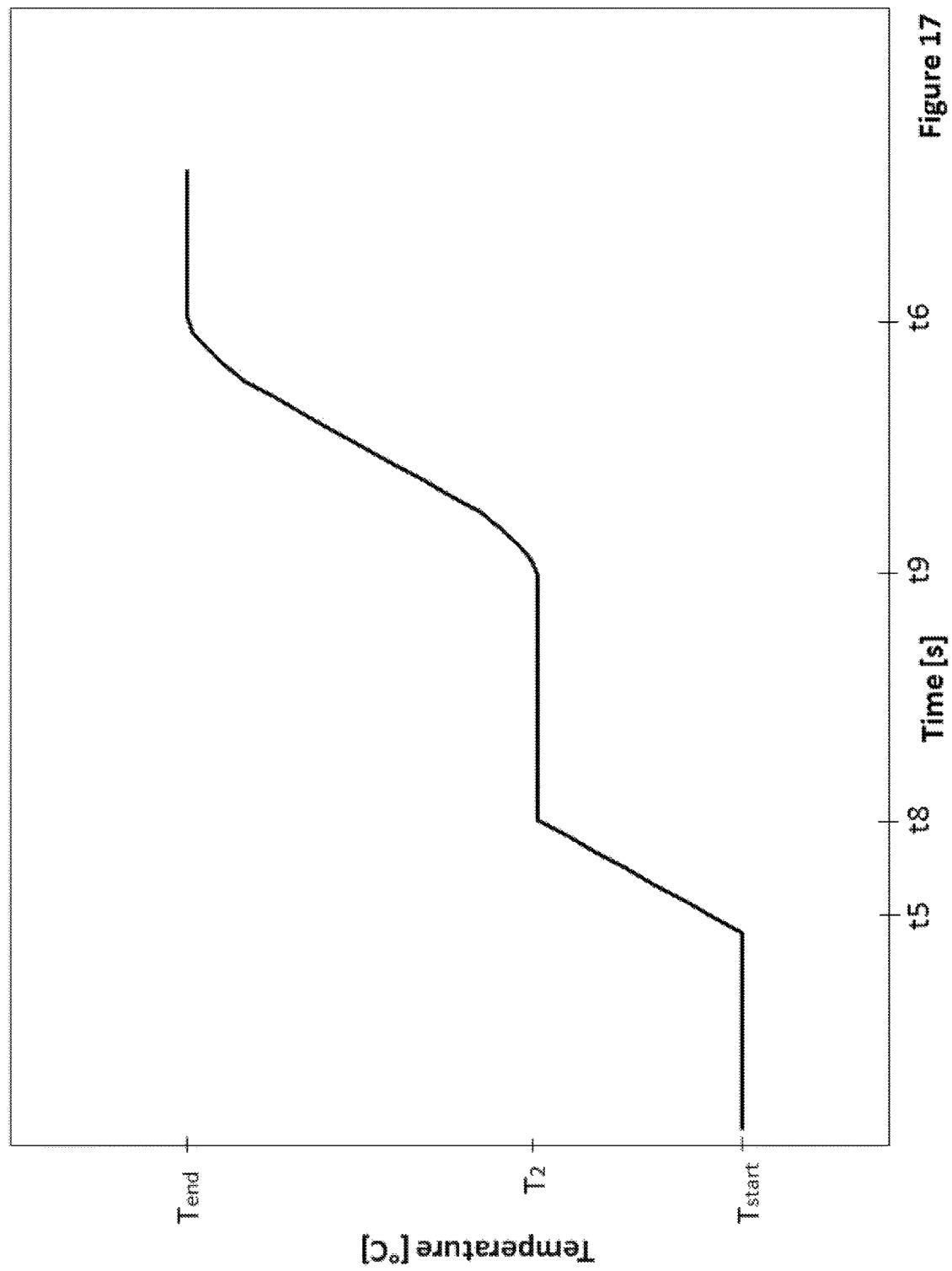
FIG. 17 shows a ninth exemplary temperature profile that may be applied to the temperature varying GC column of the invention.

Finally FIG. 17 employs three plateaus, but this time has zero gradient at the start temperature $T_{start}$ up to $t_5$ (to form the first plateau), a constant gradient between $t_5$ and $t_8$, then a zero gradient (to form the second plateau) between $t_8$ and $t_9$, a non constant gradient between $t_9$ and $t_6$ and finally a zero gradient after $t_6$ at the end temperature $T_{end}$ (to form the third plateau).

Although some specific embodiments have been described, it will be understood that these are merely for the purposes of illustration and that various modifications or alternatives may be contemplated by the skilled person. For example, although a single GC column has been described, it will be understood that the invention is equally applicable to a system involving multiple (eg, 2) GC columns. In particular, it is possible to use a second (additional) GC or LC column before any combustion or reduction etc takes place. This allows the constituents of the sample to be chromatographically separated before they are each (potentially separately) combusted, reduced or otherwise. Each set of combustion or reaction products (eg N, C or S) can then be separately analysed using the temperature variable GC column 60 described above.

It will of course be understood that the temperatures and ramping rates employed to generate the chromatograms of FIGS. 6 and 9 are exemplary in nature. In general terms, the parameters chosen (temperature(s); ramping rate(s); ramping rate profiles, ie linear, non linear or combined ramping rates; no, one, or multiple intermediate plateaus during ramping from start to finish temperatures, etc) will depend upon multiple factors such as (but not limited to) the sample to be analysed, the configuration (size, shape, phases etc) of the GC column 60, and so forth. The skilled person will have no difficulty in identifying and optimising the parameters. So, for example, although a starting temperature of 50 degrees Celsius was employed to generate the chromatogram of FIG. 6, a range of temperatures from around 35 degrees Celsius up to around 70 degrees Celsius, preferably a range of temperatures from around 45 degrees Celsius up to around 60 degrees Celsius may in fact be employed. Likewise, a range of end temperatures in FIG. 6 between around 120 and 190 degrees Celsius, preferably between around 135 degrees and 170 degrees Celsius may be used. The rate of temperature increase (indicated as 1 degree per second in FIG. 6 may be anywhere between around 0.5 degrees per second up to around 2 degrees per second. It will be understood that the rate of temperature increase needs to be correlated with the peak positions, and these are dependent upon both the sample and the GC column. Likewise in respect of FIG. 9, a range of temperature gradients between 0.5 degrees per second and 2 degrees per second is possible, the start temperature may be anywhere from around 35 degrees Celsius up to around 90 degrees Celsius, preferably anywhere from around 45 degrees Celsius up to around 70 degrees Celsius, and a range of end temperatures in FIG. 9 between around 190 and 300 degrees Celsius, preferably between around 220 and 270 degrees Celsius may be used.

The foregoing embodiments employ an EA-IRMS to generate exemplary chromatograms, in order to illustrate the effects and benefits of the invention. It is however to be understood that the invention is not limited to such a spectrometer. Other forms of elemental analyser can be used and the benefits of applying a temperature variation to a GC column during analysis may be obtained. For example, the concept may be applied to a Thermal Conductivity Detector, a Flame Photometric Detector, a Flame Ionisation Detector, an Isotope Ratio Infrared Spectrometer, any Magnetic Sector Analyzer, or a Double Focussing Sector Mass Spectrometer.

The invention claimed is:

1. A sample preparation apparatus for an elemental analysis system, comprising:
   a sample combustion and/or reduction and/or pyrolysis arrangement for receiving a sample of material to be analyzed, and producing therefrom a sample gas flow containing atoms, molecules and/or compounds including $N_2$ and $CO_2$;
   a gas chromatography (GC) column into which the continuous sample gas flow is directed;
   a heater for heating at least a part of the GC column; and
   a controller for controlling the heater;
   the controller including a timing circuitry and being configured to control the heater so as to increase the temperature of at least the part of the GC column either (1) whilst $CO_2$ in the continuous sample gas flow in the GC column elutes or (2) whilst the continuous sample gas flow in the GC column elutes and after the $N_2$ and $CO_2$ have passed the GC column.

2. The sample preparation apparatus of claim 1, further comprising a detector for detecting atoms, molecules or compounds that have passed through the GC column, and wherein the controller is configured to control the heater so that the temperature of at least the part of the GC column is increased after a first one or more species of atoms, molecules or compounds have passed the GC column.

3. The sample preparation apparatus of claim 1, further comprising a thermometer or thermocouple for monitoring a temperature of at least part of a GC column, wherein the controller is configured to control the heater so that the temperature changes substantially linearly between a start temperature $T_{start}$ and an end temperature $T_{end}$.

4. The sample preparation apparatus of claim 1, further comprising a thermometer or thermocouple for monitoring a temperature of at least part of a GC column, wherein the controller is configured to control the heater so that the temperature changes substantially non-linearly between a start temperature $T_{start}$ and an end temperature $T_{end}$.

5. The sample preparation apparatus of claim 1, further comprising a thermometer or thermocouple for monitoring a temperature of at least part of a GC column, wherein the controller is configured to control the heater so that the temperature change is partly linear and partly non linear between a start temperature $T_{start}$ and an end temperature $T_{end}$.

6. The sample preparation apparatus of claim 1, further comprising a detector for detecting atoms, molecules or compounds that have passed through the GC column and a thermometer or thermocouple for monitoring a temperature of at least part of a GC column, and wherein the controller is configured to control the heater so that the temperature of at least the part of the GC column is increased after a first one or more species of atoms, molecules or compounds have passed the GC column across a first temperature range ($T_2 - T_{start}$), and wherein $T_2 > T_{start}$.

7. The sample preparation apparatus of claim 6, wherein the controller is configured to control the heater so that the temperature of at least the part of the GC column is increased after a first one or more species of atoms, molecules or compounds have passed the GC column with substantially linearly, or substantially non-linearly, or with both linear and non-linear temperature changes, across the first temperature range ($T_2 - T_{start}$).

8. The sample preparation apparatus of claim 1, further comprising a detector for detecting atoms, molecules or compounds that have passed through the GC column and a thermometer or thermocouple for monitoring a temperature of at least part of a GC column, and wherein the controller is configured to control the heater so that the temperature in at least the part of the GC column changes across a second temperature range ($T_{end} - T_2$), and wherein $T_{end} > T_2$ before a second one or more species of atoms, molecules or compounds have passed the GC column.

9. The sample preparation apparatus of claim 8, wherein the controller is configured to control the heater so that the temperature changes substantially linearly, or substantially non-linearly, or with both linear and non-linear temperature changes, across the second temperature range ($T_{end} - T_2$) before a second one or more species of atoms, molecules or compounds have passed the GC column.

10. The sample preparation apparatus of claim 2, wherein the sample and/or reduction and/or pyrolysis arrangement is configured to generate $N_2$, and $CO_2$ or $N_2$, $CO_2$ and $SO_2$.

11. The sample preparation apparatus of claim 1, further comprising a thermometer or thermocouple for monitoring a temperature of at least part of a GC column, and wherein the controller is configured to maintain the temperature of the GC column at a first, fixed temperature $T_{start}$ during a first period of sample analysis, to ramp the temperature of the GC column from the first fixed temperature $T_{start}$ to a second, higher fixed temperature $T_{end}$ over a second period of sample analysis, and to maintain the temperature of the GC column at the second, higher fixed temperature $T_{end}$ over a third period of sample analysis.

12. The sample preparation apparatus of claim 11, wherein the controller is configured to commence the ramping the temperature of the GC column from the first temperature $T_{start}$ to the second fixed temperature $T_{end}$, at a predetermined time after combustion/reduction/pyrolysis of the sample.

13. The sample preparation apparatus of claim 11, wherein the first fixed temperature lies in the range of 35 to 90 degrees Celsius.

14. The sample preparation apparatus of claim 11, wherein the second fixed temperature $T_{end}$ is between 190 degrees Celsius and 300 degrees Celsius.

15. The sample preparation apparatus of claim 11, wherein the controller is configured to instruct the heater to cause the GC column to rise in temperature from the said first fixed temperature $T_{start}$ to the second fixed temperature $T_{end}$ over a period of around 1 to 3 minutes.

16. The sample preparation apparatus of claim 11, wherein the controller is further configured to ramp the temperature of the GC column down from the second higher fixed temperature $T_{end}$ to the first fixed temperature $T_{start}$ over a fourth period of sample analysis following the said third period of sample analysis.

17. The sample preparation apparatus of claim 16, wherein the controller is configured to instruct the heater to cause the GC column to drop in temperature from the said second fixed temperature $T_{end}$ to the first fixed temperature $T_{start}$ over a period of around 1 to 3 minutes.

18. The sample preparation apparatus of claim 17, wherein the controller is configured to commence the ramp down of temperature of the GC column from the second temperature $T_{end}$ to the first temperature $T_{start}$, at a predetermined time after the GC column has attained the said second temperature $T_{end}$ during the said third period of sample analysis.

19. A sample preparation apparatus for an elemental analysis system, comprising:
   a sample combustion and/or reduction and/or pyrolysis arrangement for receiving a sample of material to be analyzed, and producing therefrom a sample gas flow containing atoms, molecules and/or compounds including $N_2$ and $CO_2$;

a gas chromatography (GC) column into which the continuous sample gas flow is directed;

a heater for heating at least a part of the GC column; and a controller for controlling the heater;

the controller being configured to control the heater so as to increase the temperature of at least the part of the GC column either (1) whilst $CO_2$ in the continuous sample gas flow in the GC column elutes or (2) whilst the continuous sample gas flow in the GC column elutes and after the N and $CO_2$ have passed the GC column;

wherein the controller is configured to maintain the temperature of the GC column at a first, fixed temperature $T_{start}$ during a first period of sample analysis, to ramp the temperature of the GC column from the first fixed temperature $T_{start}$ to a second, higher fixed temperature $T_{end}$ over a second period of sample analysis, and to maintain the temperature of the GC column at the second, higher fixed temperature $T_{end}$ over a third period of sample analysis;

wherein the controller is further configured to ramp the temperature of the GC column down from the second higher fixed temperature $T_{end}$ to the first fixed temperature $T_{start}$ over a fourth period of sample analysis following the said third period of sample analysis;

wherein the GC column is located within a housing, and wherein the apparatus further comprises a means for directing relatively cooler gas into the housing to expel relatively warmer gas within the housing.

20. The sample preparation apparatus of claim 19, wherein the housing comprises a plurality of walls, at least some of which define an internal channel for receiving the expelled relatively warmer gas and directing it out of the housing through one or more openings therein, and wherein the means for directing relatively cooler gas into the housing comprises a fan or a pump.

21. A sample preparation apparatus for an elemental analysis system, comprising:

a sample combustion and/or reduction and/or pyrolysis arrangement for receiving a sample of material to be analyzed, and producing therefrom a sample gas flow containing atoms, molecules and/or compounds including $N_2$ and $CO_2$;

a gas chromatography (GC) column into which the continuous sample gas flow is directed;

a second GC column or a LC column wherein the sample to be analyzed and received by the sample combustion and/or reduction and/or pyrolysis arrangement has been generated by the second GC column or LC column by a chromatographic process from a sample supplied to the second GC column or LC column;

a heater for heating at least a part of the GC column; and a controller for controlling the heater;

the controller being configured to control the heater so as to increase the temperature of at least the part of the GC column either (1) whilst $CO_2$ in the continuous sample gas flow in the GC column elutes or (2) whilst the continuous sample gas flow in the GC column elutes and after the $N_2$ and $CO_2$ have passed the GC column.

* * * * *

UNITED STATES PATENT AND TRADEMARK OFFICE
CERTIFICATE OF CORRECTION

PATENT NO. : 10,332,735 B2
APPLICATION NO. : 15/690617
DATED : June 25, 2019
INVENTOR(S) : Brodie et al.

Page 1 of 1

It is certified that error appears in the above-identified patent and that said Letters Patent is hereby corrected as shown below:

In the Claims

Claim 19, Column 19, Line 13:
Replace "and after the N and $CO_2$ have passed the GC column"
With --and after the $N_2$ and $CO_2$ have passed the GC column--

Signed and Sealed this
Twenty-second Day of October, 2019

Andrei Iancu
*Director of the United States Patent and Trademark Office*